US005543413A

United States Patent [19]
Townsend et al.

[11] Patent Number: 5,543,413
[45] Date of Patent: Aug. 6, 1996

[54] HETEROCYCLIC THIOAMIDES AND RELATED ANALOGS AS ANTIVIRAL AGENTS WITH A UNIQUE MODE OF ACTION

[75] Inventors: Leroy B. Townsend; John C. Drach, both of Ann Arbor, Mich.; Thomas E. Renau, Dana Point, Calif.

[73] Assignee: Regents of the University of Michigan, Ann Arbor, Mich.

[21] Appl. No.: 357,762

[22] Filed: Dec. 15, 1994

Related U.S. Application Data

[63] Continuation of Ser. No. 201,695, Feb. 25, 1994, abandoned.
[51] Int. Cl.$^6$ .......................... C07D 487/04; A61K 31/52
[52] U.S. Cl. ............................................. 514/258; 544/280
[58] Field of Search ............................. 514/258; 544/280

[56] References Cited

U.S. PATENT DOCUMENTS

| | | | |
|---|---|---|---|
| 4,892,865 | 1/1990 | Townsend et al. | 536/24 |
| 4,927,830 | 5/1990 | Townsend et al. | 544/280 |
| 4,968,686 | 11/1990 | Townsend et al. | 544/280 |

OTHER PUBLICATIONS

Renau, T.E., et al., "Relationship between cytotoxicity and conversion of thiosangivamycin analogs to toyocamycin analogs in cell culture medium" *Biochem. Pharmacol.* (1994) 48:801–807.

Biron, K.K., et al., "Metabolic activation of the nucleoside analog 9-{[2-hydroxy-1-(hydroxymethyl)ethoxy]methyl}guanine in human diploid fibroblsts infected with human cytomegalovirus" *Proc. Natl. Acad. Sci. USA* (1985) 82:2473–2477.

Gupta, P.K., et al., "Synthesis, cytotoxicity, and antiviral activity of some acyclic analogues of the pyrrolo[2,3–d]pyrimidine nucleoside antibiotics tubercidin, toyocamycin, and sangivamycin" *J. Med. Chem.* (1989) 32:402–408.

Gupta, P.K., et al. "Synthesis, cytotoxicity, and antiviral activity of certain 7-[(2–hydroxyethoxy)methyl]pyrrol[2,3–d]pyrimidine nucleosides related to toyocamycin and sangivamycin" *J. Med. Chem.* (1989) 32:1420–1425.

Prichard, M.N., et al., "A microtiter virus yield reduction assay for the evaluation of antiviral compounds against human cytomegalovirus and herpes simplex virus" *J. Virol. Meth.* (1990) 28:101–106.

Prichard, M.N., et al., "Three–dimensional analysis of the synergistic cytotoxicity of ganciclovir and zidovudine" *Antimicrob. Agents & Chemother.* (1991) 35:1060–1065.

Renau, T.E., et al. "Antiherpetic activity, cytotoxicity and metabolism of non–nucleoside analogs related to toyocamycin, sangivamycin and thiosangivamycin" Sixth International Conference on Antiviral Research, Venice, Italy, 25–30 Apr. 1993, *Antiviral Res.*, vol. 20, Suppl. 1 (1993), p. 118 (Abstract No. 138).

Renau, T.E., et al. "Spontaneous oxidation of thiosangivamyicin analogs by cell culture medium ameliorates cytotoxicity" 206th Nationaal American Chemical Society Meeting, Chicago, IL, 22–27 Aug. 1993, *Abstr. Pap. Am. Chem. Soc.* 206 (1–2) MEDI (1993), Abstract No. 133.

Renau, T.E., et al. "Activity against human cytomegalovirus, cytotoxicity and mode of action of a non–nucleoside pyrrolo [2,3–d]pyrimidine" Seventh International Conference on Antiviral Research, Charleston, SC, Mar. 1994, Abstract No. 104 (to be published in *Antiviral Res.*).

Renau, T.E., et al. "Structure–activity relationships of non–nucleoside pyrrolopyrimidine analogs active against human cytomegalovirus" Seventh International Conference on Antiviral Research, Charleston, SC, Mar. 1994, Abstract No. 105 (to be published in *Antiviral Res.*).

Renau, T.E. et al. "Design, synthesis and activity against human cytomeglovirus of non–phosphorlatable analogs of toyocamycin, sangivamycin and thiosangivamycin" *Bioorgan. & Med. Chem. Let.* (1992) 2(12):1755–1760.

Renau, T.E., et al., "Improved synthesis and biological evaluation of an acyclic thiosangivamycin active against human cytomegalovirus" *Antiviral Res.* (1992) 19:15–28.

(List continued on next page.)

*Primary Examiner*—Mark L. Berch

[57] ABSTRACT

This invention relates to a novel class of 4,5,6,7-substituted non-nucleoside, non-phosphorylatable pyrrolo[2,3-d]pyrimidines which exhibit both significantly lower levels of cytotoxicity and superior antiviral activity than known nucleoside, non-nucleoside, and non-nucleoside, non-phosphorylatable pyrrolo[2,3-d]pyrimidine derivatives, particularly against human DNA viruses such as cytomegalovirus (HCMV) and herpes simplex virus type 1 (HSV-1). These compounds are represented by the following formula:

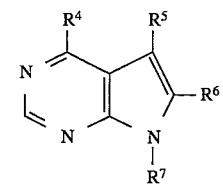

wherein
  $R^4$ is $-NH_2$ or $-NHCH_3$;
  $R^5$ is $-CN$, $-CSNH_2$, or $-CSeNH_2$;
  $R^6$ is $-H$ or $-NH_2$; and
  $R^7$ is selected from the group consisting of
    aryls and aralkyls having 6 to 30 carbon atoms;
    aliphatic oxy-hydrocarbyls having 2 to 15 carbon atoms, lacking free hydroxyl groups and further lacking acyl or acyl derivatized groups; and
    oxy-hydrocarbyls having 6 to 30 carbon atoms, at least one aryl or aralkyl group, and only one oxy-group;
  with the proviso that if $R^5$ is -CN and $R^6$ is -H then $R^4$ is $-NH_2$ and $R^7$ is $-CH_2C_6H_4-2-CH_3$.

31 Claims, 4 Drawing Sheets

OTHER PUBLICATIONS

Saxena, N.K., et al., "Synthesis and antiviral activity of some 7-[(2-hydroxyethoxy)methyl}pyrazolo[3,4-d]pyrimidine analogues of sangivamycin and toyocamycin" *J. Med. Chem.* (1990) 33:1980–1983.

Shipman, Jr., C., et al. "Evaluation of 4-(2-hydroxyethyl)-1-piperaazineëthanesulfonic acids (HEPES) as a tissue culture buffer" *Proc. Soc. Exp. Biol.* (1969) 130:305–310.

Swayze, E.E., et al., "Synthesis, atiproliferative, and antiviral evaluation of certain acyclic 6-substituted pyrrolo[2,3-d]-pyrimidine nucleoside analogs related to sangivamycin and toyocamycin" *Nucleosides & Nucleotides* (1992) 11:1507–1527.

Swayze, E.E., et al., "The improved preparation of a versatile synthon for the synthesis of pyrrolo[2,3-d]pyrimidines" *Nucleic Acid Chemistry: Improved and New Synthetic Procedures, Methods and Techniques*, Townsend, L. B., et al., eds., (1991) Wiley-Interscience, New York, Part IV, pp. 16–18.

Turk, S.R., et al. "Pyrrol[2,3-d]pyrimidine nucleosides as inhibitors of human cytomegalovirus" *Antimicrob. Agents & Chemother.* (1987) 31:544–550.

Hirsch, Sci American Apr. 1987, pp. 76–85.

Hermann, Jr., Prog. Med. Virol. 3, 158 (1961).

Collins, Ann. N.Y. Acad. Sci. 284, 49 (1977).

Sidwell, Appl. Microbiol. 22, 797 (1971).

Drach, Ann. NY Acad Sci. 284, 396 (1977).

Hu, Antiviral, Res. 11, 217 (1989).

Field, Clin. Microbiol. Rev. 7, 1–13 (1994).

Hsiung, Antiviral Res. 12, 239 (1989).

Drug Evaluations Manual (AMA 1993), p. 1723.

a: R= CH₂OCH₂CH₃           f: R= CH₂C₆H₄-3-CH₃
b: R= CH₂O(CH₂)₂OCH₃       g: R= CH₂C₆H₄-2-CH₃
c: R= CH₂OCH₂C₆H₅          h: R= CH₂C₆H₄-4-C(CH₃)₃
d: R= CH₂C₆H₅              i: R= CH₂C₆H₄-4-OCH₃
e: R= CH₂C₆H₄-4-CH₃ i.  1) CH(OEt)₃, CH₃CN; 2) NaH, RX, CH₃CN.
ii. NH₃/MeOH.
iii. H₂, Pd/C, EtOAc/EtOH.
iv. MeOH, H₂S/NaOMe.
v.  MeOH, H₂Se/NaOMe.

a: R= $CH_2OCH_2CH_3$ b: R= $CH_2OCH_2CH_2OCH_3$ i. $NaNO_2$, $H_2O$/AcOH.

ii. $POCl_3$.

iii. $H_2NCH_3$.

iv. $NaOCH_3$, $CH_3OH$, $H_2S$.

a: R= CH₂OCH₂CH₃ b: R= CH₂OCH₂CH₂OCH₃ c: R= CH₂OCH₂C₆H₅ i. NH₃ (liq).

ii. NaOMe, MeOH, H₂S.

HETEROCYCLIC THIOAMIDES AND RELATED ANALOGS AS ANTIVIRAL AGENTS WITH A UNIQUE MODE OF ACTION

REFERENCE TO GOVERNMENT SUPPORT

This invention was made in part with Government support under contract number NO1-AI72641 awarded by the National Institute of Allergy and Infectious Diseases. The Government has certain rights in this invention.

RELATED APPLICATIONS

This application is a continuation of U.S. patent application Ser. No. 08/201,695, filed Feb. 25, 1994, now abandoned.

TECHNICAL FIELD

The present invention relates to new non-phosphorylatable, non-nucleoside pyrrolo[2,3-d]pyrimidines and their use in the treatment of viral infections. More particularly, the present invention relates to certain pyrrolo[2,3-d]pyrimidines that exhibit antiviral activity against human cytomegalovirus (HCMV) and herpes simplex virus type 1 (HSV-1).

BACKGROUND ART

Broad spectrum antiviral activity of pyrrolo[2,3-d]pyrimidine nucleosides such as tubercidin, sangivamycin and toyocamycin and some substituted derivatives has been previously reported. Activity of those compounds against specific viruses, such as RNA rhinovirus and DNA herpes simplex virus type 1 and type 2 has also been reported. See, for example, Bergstrom, D. E. et al., *J. Med. Chem.* 27:285–292 (1984); and DeClercq, E. et al., *Antimicrob. Agents Chemother.*, 29:482–487 (1986).

Pyrrolo[2,3-d]pyrimidine nucleosides are particularly attractive as potential antiviral agents because of their stability toward the action of two major enzymes of bioactive purine nucleoside inactivation, deamination by adenosine deaminase and glycosidic bond cleavage by purine nucleoside phosphorylases. Unfortunately, many of the pyrrolo[2,3-d]pyrimidine nucleosides which have been previously described as having potential antiviral activity also exhibit unacceptable levels of cytotoxicity, thereby diminishing their usefulness in treatment of viral infections.

A number of pyrrolo[2,3-d]pyrimidine nucleoside derivatives which exhibit improved antiviral activity and more acceptable levels of cytotoxicity than tubercidin, sangivamycin, toyocamycin and thiosangivamycin have been reported. These prior art pyrrolo[2,3-d]pyrimidine nucleoside derivatives are described below.

Townsend et al. (U.S. Pat. No. 4,892,865) disclose the use of, inter alia, several 4-amino-pyrrolo[2,3-d]pyrimidine-5-carbonitriles and 4-aminopyrrolo [2,3-d]pyrimidine-5-thiocarboxamides substituted at the 7-position with 2',3'-dideoxy-2',3'-didehydro-β-D-ribofuranose and 2',3'-dideoxyribofuranose as antiviral agents.

Renau et al. (*Bioorg. & Med. Chem. Lett.*, 2:1755–1760, 1992) disclose the use of, inter alia, 4-amino-pyrrolo[2,3-d]pyrimidine -5-thiocarboxamides and 4-amino-pyrrolo[ 2,3-d]pyrimidine-5-carbonitriles substituted at the 7-position with β-D-ribofuranose as antiviral agents.

A number of pyrrolo[2,3-d]pyrimidine non-nucleoside derivatives which exhibit improved antiviral activity and more acceptable levels of cytotoxicity than tubercidin, sangivamycin, toyocamycin and thiosangivamycin as well as the nucleoside derivatives described above have been reported. These prior art pyrrolo[2,3-d]pyrimidine non-nucleoside derivatives are described below.

Townsend et al. (U.S. Pat. Nos. 4,927,830 and 4,968,686) disclose the use of, inter alia, several 4-amino-pyrrolo[2,3-d]pyrimidine-5-thiocarboxamides and 4,6-diamino-pyrrolo [2,3-d]pyrimidine-5 -thiocarboxamides variously substituted at the 7-position with -CH$_2$OCH(CH$_2$OH)$_2$, -CH$_2$OCH$_2$CH$_2$OH and -CH(CH$_2$OH)(OCH(CH$_2$OH)$_2$) as antiviral agents.

Gupta et al. (*J. Med. Chem.*, 32: 402–408, 1989) disclose the use of, inter alia, several 4-amino-pyrrolo[2,3-d]pyrimidine-5-thiocarboxamides and 4-amino-pyrrolo[ 2,3-d]pyrimidine- 5-carbonitriles variously substituted at the 7-position by -CH$_2$OCH(CH$_2$OH)$_2$ and -CH(CH$_2$OH)(OCH(CH$_2$OH)$_2$) as antiviral agents.

Gupta et al. (*J. Med. Chem.*, 32:1420–1425, 1989) disclose the use of, inter alia, several 4-amino.-pyrrolo[2,3-d]pyrimidine-5-thiocarboxamides and 4-amino-pyrrolo[2,3-d]pyrimidine-5-carbonitriles substituted at the 7-position by -CH$_2$OCH$_2$CH$_2$OH as antiviral agents.

Renau et al. (*Antiviral Res.*, 19:15–28, 1992) disclose the use of 4-amino-pyrrolo[2,3-d]pyrimidine-5-thiocarboxamide and 4-aminopyrrolo[2,3-d]pyrimidine-5-carbonitrile substituted at the 7-position by -CH$_2$OCH$_2$CH$_2$OH as antiviral agents.

Swayze et al. (*Nucleosides and Nucleosides*, 11:1507–1527, 1992) disclose the use of, inter alia, ,4,6-diamino-pyrrolo[2,3-d]pyrimidine -5-thiocarboxamides and 4,6-diamino-pyrrolo[2,3-d]pyrimidine-5carbonitriles variously substituted at the 7-position by -CH$_2$OCH$_2$CH$_2$OH and -CH$_2$OCH(CH$_2$OH)$_2$ as antiviral agents.

Renau et al. (*Bioorg. &Med. Chem. Lett.*, 2:1755–1760, 1992) disclose the use of, inter alia, several 4-amino-pyrrolo [2,3-d]pyrimidine -5-thiocarboxamides and 4-amino-pyrrolo[ 2,3-d]pyrimidine-5-carbonitriles variously substituted at the 7-position with -CH$_2$OCH$_2$CH$_2$OH and -CH$_2$OCH(CH$_2$OH)$_2$ as antiviral agents.

A limited number of pyrrolo[2,3-d]pyrimidine non-nucleoside, non-phosphorylatable derivatives which exhibit improved antiviral activity and more acceptable levels of cytotoxicity than tubercidin, sangivamycin, toyocamycin and thiosangivamycin as well as the nucleoside derivatives described above have been reported. These prior art non-nucleoside, non-phosphorylatable derivatives are described below.

Renau et al. (*Bioorg. & Med. Chem. Lett.*, 2:1755–1760, 1992) disclose the use of, inter alia, several 4-amino-pyrrolo [2,3-d]pyrimidine -5-thiocarboxamides and 4-amino-pyrrolo[ 2,3-d]pyrimidine-5-carbonitriles variously substituted at the 7-position with -CH$_3$, -CH$_2$CH=CH$_2$, -CH$_2$CH$_2$CH$_3$ as antiviral agents.

DISCLOSURE OF THE INVENTION

One aspect of the present invention relates to a novel class of 4,5,6,7-substituted non-nucleoside, non-phosphorylatable pyrrolo[2,3-d]pyrimidines which exhibit both significantly lower levels of cytotoxicity and superior antiviral activity than known nucleoside, non-nucleoside, and non-nucleoside, non-phosphorylatable pyrrolo[ 2,3-d]pyrimidine derivatives, particularly against human DNA viruses such as cytomegalovirus (HCMV) and herpes simplex virus type 1 (HSV-1). These compounds are represented by the following formula:

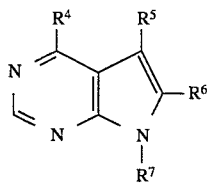

wherein $R^4$ is -$NH_2$ or -$NHCH_3$;

$R^5$ is -CN, -$CSNH_2$, or -$CSeNH_2$;

$R^6$ is -H or -$NH_2$; and $R^7$ is selected from the group consisting of aryls and aralkyls having 6 to 30 carbon atoms;

aliphatic oxy-hydrocarbyls having 2 to 15 carbon atoms, lacking free hydroxyl groups and further lacking acyl or acyl derivatized groups; and oxy-hydrocarbyls having 6 to 30 carbon atoms, at least one aryl or aralkyl group, and only one oxy-group;

with the proviso that if $R^5$ is -CN and $R^6$ is -H then $R^4$ is -$NH_2$ and $R^7$ is -$CH_2C_6H_4$-2-$CH_3$.

The invention also includes pharmaceutically acceptable salts and derivatives, such as esters, of the above-described compounds [*Remington's Pharmaceutical Sciences*, Mack Publishing Co., Easton, Pa. (latest edition)].

Another aspect of the invention is a method for treating a viral infection in an animal patient comprising administering a therapeutically effective amount of one or more of the above-described compounds to the patient.

Still another aspect of the invention is a pharmaceutical composition for treating viral infections comprising a therapeutically effective amount of one or more of the above-described compounds and a pharmaceutically acceptable carrier.

DETAILED DESCRIPTION OF THE INVENTION

A. Chemical Structure of the Compounds

Figure 1:
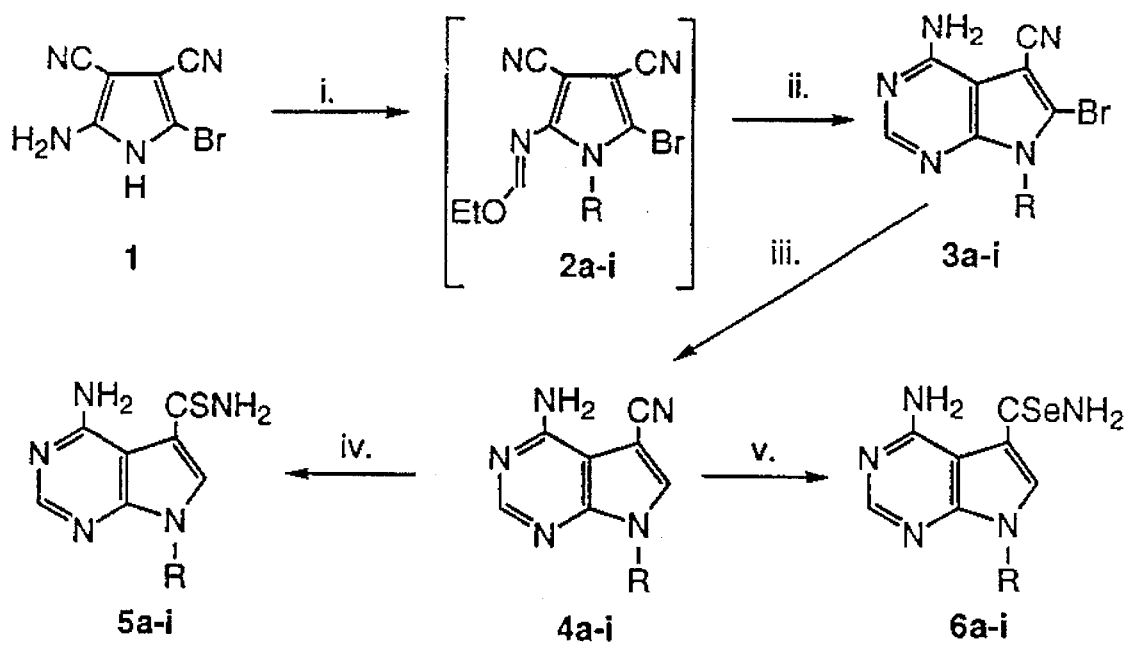
FIG. 1 is a flow chart that illustrates the synthetic route for the preparation of the N-7 substituted non-nucleoside analogs (compounds 4g, 5a–i, 6a–i).

The term "nucleoside derivative" as used herein relates to pyrrolo[2,3-d]pyrimidine compounds which have a modified but intact furan ring at N-7 ($R^7$). Examples include 2',3'-dideoxy-2',3'-didehydro -β-D-ribofuranose and 2',3'-dideoxy-β-D-ribofuranose.

The term "non-nucleoside derivative" as used herein relates to pyrrolo[2,3-d]pyrimidine compounds which do not have a modified or intact furan ring at N-7 ($R^7$) but are substituted at $R^7$ instead with a radical having an available (or free) -OH (hydroxyl) group which can be phosphorylated to result in an active metabolite. Examples of such substituents include $CH_2OCH(CH_2OH)_2$ and $CH_2OCH_2CH_2OH$.

The term "non-nucleoside, non.-phosphorylatable derivative" as used herein relates to pyrrolo[2,3-d]pyrimidine compounds which do not have a modified or intact furan ring at N-7 ($R^7$) and are not substituted at $R^7$ with a radical having an available -OH (hydroxyl) group and thereby cannot be phosphorylated to an active metabolite. Examples of such substituents include various aryl, aralkyl, and oxy-hydrocarbyl radicals.

The terms "thioamide" and "thiocarboxamide" are used synonymously herein. Similarly, the terms "nitrile" and "carbonitrile" are used synonymously herein. The terms "selenamide" and "selenocarboxamide" are used synonymously herein to denote compounds having a -$CSeNH_2$ group.

The term "aryl" as used herein is generic to monocyclic aromatic radicals which may be unsubstituted, substituted, or multiply substituted. Examples of such substituents include -$CH_3$, -$CH_2CH_3$, -$C(CH_3)_3$, -$OCH_3$, and -$OCH_2CH_3$. Examples of aryls include -$C_6H_5$, methylphenyl (such as -$C_6H_4$-2-$CH_3$, -$C_6H_4$-3-$CH_3$, and -$C_6H_4$-4-$CH_3$), dimethylphenyl (such as 2,3-dimethylphenyl, 2,4-dimethylphenyl, 2,5-dimethylphenyl, and the like), trimethylphenyl (such as 2,4,6-trimethylphenyl and the like), methoxyphenyl (such as -$C_6H_4$-2-$OCH_3$, -$C_6H_4$-3-$OCH_3$, and -$C_6H_4$-4-$OCH_3$), dimethoxyphenyl (such as 2,3-dimethoxyphenyl, 2,4-dimethoxyphenyl, 2,5-dimethoxyphenyl, and the like), (tert-butyl)phenyl (such as -$C_6H_4$-2-$C(CH_3)_3$, -$C_6H_4$-3-$C(CH_3)_3$, and -$C_6H_4$-4-$C(CH_3)_3$), di(tert-butyl)phenyl (such as 2,3-di(tert-butyl)phenyl, 2,4-di(tert-butyl)phenyl, 2,5-di(tert-butyl)phenyl, and the like), methoxymethylphenyl (such as 4-methoxy-2-methylphenyl and the like), and tert-butylmethylphenyl (such as 4-(tert-butyl)-2-methylphenyl and the like).

The term "aralkyl" as used herein is generic to alkyl radicals having an aryl group. Examples of aralkyls include -$CH_2C_6H_5$, methylbenzyl (such as -$CH_2$-$C_6H_4$-2-$CH_3$, -$CH_2$-$C_6H_4$-3-$CH_3$, -$CH_2$-$C_6H_4$-4-$CH_3$), dimethylbenzyl (such as 2,3-dimethylbenzyl, 2,4-dimethylbenzyl, 2,5-dimethylbenzyl, and the like), methoxybenzyl (such as -$CH_2$-$C_6H_4$-2-$OCH_3$, -$CH_2$-$C_6H_4$-3-$OCH_3$, -$CH_2$-$C_6H_4$-4-$OCH_3$), dimethoxybenzyl (such as 2,3-dimethoxybenzyl, 2,4-dimethoxybenzyl, 2,5-dimethoxybenzyl, and the like), (tert-butyl)benzyl (such as -$CH_2$-$C_6H_4$-2-$C(CH_3)_3$, -$CH_2$-$C_6H_4$-3-$C(CH_3)_3$, -$CH_2$-$C_6H_4$-4-$C(CH_3)_3$), di(tert-butyl)benzyl (such as ? ,3-di(tert-butyl)benzyl, 2,4-di(tert-butyl)benzyl, 2,5-di(tert-butyl)benzyl, and the like), methoxymethylbenzyl (such as 4-methoxy-2-methylbenzyl and the like), tert-butylmethylbenzyl (such as 4-(tert-butyl)-2-methylbenzyl and the like), phenylethyl (such as 1-phenylethyl and 2-phenylethyl), phenylpropyl (such as 3-phenylpropyl and the like), and methoxyphenylethyl (such as 2-(2-methoxyphenyl)ethyl and the like).

The term "hydrocarbyl" as used herein is generic to radicals derived from hydrocarbons. The term "oxy-hydrocarbyl" as used herein is generic to hydrocarbyl radicals having at least one oxy-group. The term "oxy-group" as used herein is generic to R-O-R linkages, excluding those arising from substituents on aryl groups. Examples of oxy-groups include -CH$_2$-O-CH$_2$-, -CH$_2$-O-C$_6$H$_4$-, and -CH$_2$-O-CH(CH$_3$)-, but not -C$_6$H$_4$-2-OCH$_3$.

The term "aliphatic" as used herein is generic to linear, branched, or multiply-branched acyclic species.

Examples of acyl or acyl derivatized groups include -C(=O)H, -C(=O)R, -C(=O)OH, -C(=O)OR, -C(=O)NHR, and the like.

Examples of aliphatic oxy-hydrocarbyls having 2 to 15 carbon atoms, lacking free hydroxyl groups and further lacking acyl or acyl derivatized groups include -CH$_2$-O-CH$_3$, -CH$_2$-O-CH$_2$CH$_3$, -CH$_2$-O-CH$_2$CH$_2$CH$_3$, -CH$_2$-O-CH$_2$CH$_2$-O-CH$_3$, -CH$_2$-O-CH$_2$CH$_2$-O-CH$_2$CH$_3$, -CH$_2$-O-CH$_2$CH$_2$-O-CH$_2$CH$_2$-O-CH$_3$, -CH$_2$-CH$_2$-O-CH$_3$, -CH$_2$-CH$_2$-O-CH$_2$CH$_3$, -CH$_2$-O-CH(CH$_2$OCH$_3$)$_2$, -CH$_2$-O-CH(CH$_2$OCH$_2$CH$_3$)$_2$, -CH(CH$_2$OCH$_3$)-O-CH(CH$_2$OCH$_3$)$_2$, and the like.

Examples of oxy-hydrocarbyls having 6 to 30 carbon atoms, at least one aryl or aralkyl group, and only one oxy-group include -CH$_2$-O-C$_6$H$_5$, -CH$_2$-O-CH$_2$C$_6$H$_5$, -CH$_2$-CH$_2$-O-C$_6$H$_5$, -CH$_2$-CH$_2$-O-CH$_2$C$_6$H$_5$, (methylphenyloxy)methyl (such as (4-methylphenyloxy)methyl and the like), (methylbenzyloxy)methyl (such as (4-methylbenzyloxy)methyl and the like), (methoxyphenyloxy)methyl (such as (4-methoxyphenyloxy)methyl and the like), (methoxybenzyloxy)methyl (such as (4-methoxybenzyloxy)methyl and the like), (tert-butylphenyloxy)methyl (such as (4-tert-butylphenyloxy)methyl and the like), (tert-butylbenzyloxy)methyl (such as (4-butylbenzyloxy)methyl and the like), [(methoxy) (methyl)phenyloxy]methyl (such as (4-methoxy-2-methylphenyloxy)methyl and the like), and [(methoxy)(methyl)benzyloxy]methyl (such as (4-methoxy-2-methylbenzyloxy)methyl and the like).

When R$^7$ represents an aryl or aralkyl radical, it is preferably selected from the group consisting of -CH$_2$C$_6$H$_5$, -CH$_2$C$_6$H$_4$-4-CH$_3$, -CH$_2$C$_6$H$_4$-3-CH$_3$, -CH$_2$C$_6$H$_4$-2-CH$_3$, -CH$_2$C$_6$H$_4$-4-C(CH$_3$)$_3$, and -CH$_2$C$_6$H$_4$-4-OCH$_3$.

When R$^7$ represents an aliphatic oxy-hydrocarbyl radical having 2 to 15 carbon atoms, lacking free hydroxyl groups and further lacking acyl or acyl derivatized groups, and it is preferably selected from the group consisting of -CH$_2$OCH$_2$CH$_3$ and -CH$_2$O(CH$_2$)$_2$OCH$_3$.

When R$^7$ represents an oxy-hydrocarbyl radical having 6 to 30 carbon atoms, at least one aralkyl group, and only one oxy-group, it is preferably -CH$_2$OCH$_2$C$_6$H$_5$.

In a preferred embodiment, R$^5$ is -CN or -CSNH$_2$. In another embodiment, R$^4$ is -NH$_2$ or -NHCH$_3$, R$^5$ is -CSNH$_2$ or -CSeNH$_2$, and R$^6$ is -H or -NH$_2$. In yet another embodiment, R$^4$ is -NH$_2$ or -NHCH$_3$, R$^5$ is -CSNH$_2$, R$^6$ is -H or -NH$_2$. In still another embodiment, R$^4$ is -NH$_2$ or -NHCH$_3$, R$^5$ is -CSNH$_2$, and R$^6$ is -H. In still another embodiment, R$^4$ is -NH$_2$, R$^5$ is -CSNH$_2$, and R$^6$ is -H or -NH$_2$. In still another embodiment R$^4$ is -NH$_2$, R$^5$ is -CSNH$_2$, and R$^6$ is -NH$_2$. In still another embodiment, R$^4$ is -NH$_2$, R$^5$ is -CSNH$_2$, and R$^6$ is -H. In still another embodiment, R$^4$ is -NH$_2$ or -NHCH$_3$, R$^5$ is -CN, and R$^6$ is -NH$_2$. In still another embodiment, R$^4$ is -NH$_2$, R$^5$ is -CN, and R$^6$ is -NH$_2$.

Compounds of the invention include the following: 4,6-diamino-7-(ethoxymethyl)pyrrolo[ 2,3-d]pyrimidine-5-carbonitrile; 4, 6-diamino-7-[ (2-methoxyethoxy)methyl] pyrrolo[ 2,3-d]pyrimidine -5-carbonitrile; 4,6-diamino-7-(benzyloxymethyl)pyrrolo[ 2,3-d]pyrimidine-5-carbonitrile;
4, 6-diamino- 7-(benzyl)pyrrolo[2,3-d]pyrimidine- 5- carbonitrile;
4, 6-diamino- 7-(4-methylbenzyl}pyrrolo[ 2,3-d]pyrimidine- 5- carbonitrile;
4, 6-diamino- 7-(3-methylbenzyl)pyrrolo[ 2,3-d]pyrimidine-5-carbonitrile;
4,6-diamino-7-(2-methylbenzyl)pyrrolo[ 2,3-d]pyrimidine-5-carbonitrile;
4, 6-diamino-7-(4-tert-butylbenzyl)pyrrolo[ 2,3-d]pyrimidine-5-carbonitrile;
4, 6-diamino-7-(4-methoxybenzyl)pyrrolo[ 2,3-d]pyrimidine-5-carbonitrile;
4-methylamino-6-amino-7-(ethoxymethyl)pyrrolo[ 2,3-d] pyrimidine -5-carbonitrile;
4-methylamino-6-amino- 7-[ (2-methoxyethoxy)methyl] pyrrolo[ 2,3-d]pyrimidine -5-carbonitrile;
4-methylamino-6-amino-7-(benzyloxymethyl)pyrrolo[ 2,3-d]pyrimidine-5-carbonitrile;
4-methylamino-6-amino- 7-(benzyl)pyrrolo[ 2,3-d]pyrimidine- 5-carbonitrile;
4-methylamino-6-amino- 7-(4-methylbenzyl)pyrrolo[ 2,3-d] pyrimidine -5-carbonitrile;
4-methylamino-6-amino- 7-(3-methylbenzyl)pyrrolo[ 2,3-d] pyrimidine -5-carbonitrile;
4-methylamino-6-amino- 7-(2-methylbenzyl)pyrrolo[ 2,3-d] pyrimidine -5-carbonitrile;
4-methylamino-6-amino-7-(4-tert-butylbenzyl)Pyrrolo[ 2,3-d]pyrimidine -5-carbonitrile;
4-methylamino-6-amino-7-(4-methoxybenzyl)Pyrrolo[ 2,3-d]pyrimidine -5-carbonitrile;
4-amino- 7-(2-methylbenzyl)pyrrolo[ 2,3-d]pyrimidine-5-carbonitrile;
4-amino-7-(ethoxymethyl)pyrrolo[ 2,3-d]pyrimidine-5-thiocarboxamide;
4-amino-7-[ (2-methoxyethoxy)methyl]pyrrolo[2,3-d]pyrimidine -5-thiocarboxamide;
4-amino- 7-(benzyloxymethyl)pyrrolo[ 2,3-d]pyrimidine-5-thiocarboxamide;
4-amino- 7-(benzyl)pyrrolo[ 2,3-d]pyrimidine-5-thiocarboxamide;
4-amino-7-(4-methylbenzyl)pyrrolo[ 2,3-d]pyrimidine-5-thiocarboxamide;
4-amino- 7-(3-methylbenzyl )pyrrolo[ 2, :3-d]pyrimidine-5-thiocarboxamide;
4-amino- 7- (2-methylbenzyl) pyrrolo [ 2,3-d] pyrimidine-5- thiocarboxamide;
4-amino- 7-(4-tert-butylbenzyl)pyrrolo[ 2,3-d]pyrimidine-5-thiocarboxamide;
4-amino- 7-(4-methoxybenzyl)pyrrolo[ 2,3-d]pyrimidine-5-thiocarboxamide;
4-methylamino-7-(ethoxymethyl)pyrrolo[ 2,3-d]pyrimidine -5-thiocarboxamide;
4-methylamino-7-[ (2-methoxyethoxy)methyl]pyrrolo[ 2,3-d]pyrimidine -5-thiocarboxamide;
4-methylamino- 7-(benzyloxymethyl)pyrrolo[ 2,3-d]pyrimidine -5-thiocarboxamide;
4-methylamino-7-(benzyl)pyrrolo[ 2,3-d]pyrimidine-5-thiocarboxamide;
4-methylamino-7-(4-methylbenzyl)pyrrolo[ 2,3-d]pyrimidine -5-thiocarboxamide;
4-methylamino- 7-(3-methylbenzyl)pyrrolo[ 2,3-d]pyrimidine -5-thiocarboxamide;
4-methylamino-7-(2-methylbenzyl)pyrrolo[ 2,3-d]pyrimidine -5-thiocarboxamide;
4-methylamino- 7-(4- tert-butylbenzyl)pyrrolo[ 2,3-d]pyrimidine -5-thiocarboxamide;
4-methylamino- 7- (4-methoxybenzyl) pyrrolo [ 2,3-d] pyrimidine -5-thiocarboxamide;
4, 6-diamino- 7-(ethoxymethyl]pyrrolo[ 2,3-d]pyrimidine-5-thiocarboxamide;
4, 6-diamino- 7-[ (2-methoxyethoxy)methyl]pyrrolo[ 2,3-d] pyrimidine -5- thiocarboxamide;

4,6-diamino-7-(benzyloxymethyl) pyrrolo [2,3-d]pyrimidine -5-thiocarboxamide;
4,6-diamino-7-(benzyl)pyrrolo[2,3-d]pyrimidine-5-thiocarboxamide;
4,6-diamino-7-(4-methylbenzyl) pyrrolo [2,3-d] pyrimidine -5-thiocarboxamide;
4,6-diamino-7-(3-methylbenzyl)pyrrolo[2,3-d]pyrimidine -5-thiocarboxamide;
4,6-diamino-7-(2-methylbenzyl)pyrrolo[2,3-d]pyrimidine -5-thiocarboxamide;
4,6-diamino-7-(4-tert-butylbenzyl)pyrrolo[2,3-d]pyrimidine -5-thiocarboxamide;
4,6-diamino-7-(4-methoxybenzyl)pyrrolo[2,3-d]pyrimidine -5-thiocarboxamide;
4-methylamino-6-amino-7-(ethoxymethyl)pyrrolo[2,3-d]pyrimidine -5-thiocarboxamide;
4-methylamino-6-amino-7-[(2-methoxyethoxy)methyl]pyrrolo[2,3-d]pyrimidine -5-thiocarboxamide;
4-methylamino-6-amino-7-(benzyloxymethyl)pyrrolo[2,3-d]pyrimidine -5- thiocarboxamide;
4-methylamino-6-amino-7-(benzyl)pyrrolo[2,3-d]pyrimidine -5-thiocarboxamide;
4-methylamino-6-amino-7-(4-methylbenzyl)pyrrolo[2,3-d]pyrimidine -5-thiocarboxamide;
4-methylamino-6-amino-7-(3-methylbenzyl)pyrrolo[2,3-d]pyrimidine -5-thiocarboxamide;
4-methylamino-6-amino-7-(2-methylbenzyl) pyrrolo[2,3-d]pyrimidine -5-thiocarboxamide;
4-methylamino-6-amino-7-(4-tert-butylbenzyl)pyrrolo[2,3-d]pyrimidine -5-thiocarboxamide;
4-methylamino-6-amino-7-(4-methoxybenzyl)pyrrolo[2,3-d]pyrimidine -5-thiocarboxamide;
4-amino-7-(ethoxymethyl)pyrrolo[2,3-d]pyrimidine-5-selenocarboxamide;
4-amino-7-[(2-methoxyethoxy)methyl]pyrrolo[2,3-d]pyrimidine -5-selenocarboxamide;
4-amino-7-(benzyloxymethyl)pyrrolo [.2,3-d]pyrimidine -5-selenocarboxamide;
4-amino-7-(benzyl)pyrrolo[2,3-d]pyrimidine-5-selenocarboxamide;
4-amino-7-(4-methylbenzyl)pyrrolo[2,3-d]pyrimidine-5-selenocarboxamide;
4-amino-7-(3-methylbenzyl)pyrrolo[2,3-d]pyrimidine-5-selenocarboxamide;
4-amino-7-(2-methylbenzyl)pyrrolo[2,3-d]pyrimidine-5-selenocarboxamide;
4-amino-7-(4-tert-butylbenzyl)pyrrolo[2,3-d]pyrimidine -5-selenocarboxamide;
4-amino-7-(4-methoxybenzyl)pyrrolo[2,3-d]pyrimidine -5-selenocarboxamide;
4-methylamino-7-(ethoxymethyl)pyrrolo[2,3-d]pyrimidine -5-selenocarboxamide;
4-methylamino-7-[(2-methoxyethoxy)methyl]pyrrolo[2,3-d]pyrimidine -5-selenocarboxamide;
4-methylamino-7-(benzyloxymethyl)pyrrolo[2,3-d]pyrimidine -5-selenocarboxamide;
4-methylamino-7-(benzyl)pyrrolo[2,3-d]pyrimidine-5-selenocarboxamide;
4-methylamino-7-(4-methylbenzyl)pyrrolo[2,3-d]pyrimidine -5-selenocarboxamide;
4-methylamino-7-(3-methylbenzyl) pyrrolo [2,3-d] pyrimidine -5-selenocarboxamide;
4-methylamino-7-(2-methylbenzyl)pyrrolo[2,3-d]pyrimidine -5-selenocarboxamide;
4-methylamino-7-(4-tert-butylbenzyl)pyrrolo[2,3-d]pyrimidine -5-selenocarboxamide;
4-methylamino-7-(4-methoxybenzyl)pyrrolo[2,3-d]pyrimidine -5-selenocarboxamide;
4,6-diamino-7-(ethoxymethyl)pyrrolo[2,3-d]pyrimidine -5-selenocarboxamide;
4,6-diamino-7-[(2-methoxyethoxy)methyl]pyrrolo[2,3-d]pyrimidine -5-selenocarboxamide;
4,6-diamino-7-(benzyloxymethyl)pyrrolo[2,3-d]pyrimidine -5-selenocarboxamide;
4,6-diamino-7-(benzyl)pyrrolo [2,3-d]pyrimidine-5-selenocarboxamide;
4,6-diamino-7-(4-methylbenzyl)pyrrolo[2,3-d]pyrimidine -5-selenocarboxamide;
4,6-diamino-7-(3-methylbenzyl)pyrrolo[2,3-d]pyrimidine -5-selenocarboxamide;
4,6-diamino-7-(2-methylbenzyl)pyrrolo[2,3-d]pyrimidine -5-selenocarboxamide;
4,6-diamino-7-(4-tert-butylbenzyl)pyrrolo [2,3-d]pyrimidine -5-selenocarboxamide;
4,6-diamino-7-(4-methoxybenzyl)pyrrolo[2,3-d]pyrimidine -5-selenocarboxamide;
4-methylamino-6-amino-7-(ethoxymethyl)pyrrolo[2,3-d]pyrimidine -5-selenocarboxamide;
4-methylamino-6-amino-7-[(2-methoxyethoxy)methyl]pyrrolo[2,3-d]pyrimidine -5-selenocarboxamide;
4-methylamino-6-amino-7-(benzyloxymethyl)pyrrolo[2,3-d]pyrimidine -5-selenocarboxamide;
4-methylamino-6-amino-7-(benzyl)pyrrolo[2,3-d]pyrimidine -5-selenocarboxamide;
4-methylamino-6-amino-7-(4-methylbenzyl)pyrrolo[2,3-d]pyrimidine -5-selenocarboxamide;
4-methylamino-6-amino-7-(3-methylbenzyl)pyrrolo[2,3-d]pyrimidine -5-selenocarboxamide;
4-methylamino-6-amino-7-(2-methylbenzyl)pyrrolo[2,3-d]pyrimidine -5-selenocarboxamide;
4-methylamino-6-amino-7-(4-;tert-butylbenzyl)pyrrolo[2,3-d]pyrimidine -5-selenocarboxamide; and
4-methylamino-6-amino-7-(4-methoxybenzyl)pyrrolo[2,3-d]pyrimidine -5-selenocarboxamide.

B. Formulation and Use of Compounds

The compounds of the present invention exhibit superior antiviral activity and acceptable cytotoxicity for use as therapeutic agents for treating viral infections. In particular, it has been found that these compounds are effective against HCMV and HSV-1 as well as other viruses.

In this regard it will also be appreciated that "treatment" in accordance with the present invention encompasses the treatment of viral infections, as well as prophylactic treatment of patients who are at risk for viral infection, e.g. immuno-compromised patients, such as bone marrow transplant patients.

A partial list of mammalian viruses contemplated to be treatable with the compounds of the present invention includes: herpes simplex virus types 1 and 2; human cytomegalovirus; human immunodeficiency virus; human herpesvirus 6 (HHV6); varicella-zoster virus; Epstein-Barr virus (EBV); herpesvirus simiae; equine herpesvirus -1, 2 and 3; neurolymphomatosis (Marek's disease); influenza viruses A, B and C; parainfluenza viruses -1,2, 3 and 4; adenovirus; reovirus; respiratory syncytial virus; rhinovirus; coxsackle virus; echo virus; rubeola virus; hepatitis viruses; and papovavirus.

Mode of action studies with one of the most promising new compounds, 4-amino-7-[(2-methoxyethoxy)methyl] pyrrolo[2,3-d]pyrimidine -5-thiocarboxamide (denoted compound 5b herein), establish that it does not act by inhibition of DNA synthesis or other viral functions which occur in mid to late times in the viral replication cycle. Instead, the compound acts by a unique mechanism early in the viral replication cycle.

The compounds and compositions of the present invention can be used in the manufacture of medicaments and in antiviral treatment of humans and other animals by administration in accordance with conventional procedures, such as an active ingredient in pharmaceutical compositions. Techniques and formulations may be found, for example, in *Remington's Pharmaceutical Sciences,* Mack Publishing Co., Easton, Pa. (latest edition).

The pharmaceutical compositions containing the invention compounds can be administered topically, orally, or parentally and may take the form of tablets, lozenges, granules, capsules, pills, ampoules or suppositories. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the, active ingredient, may be administered for therapy by any suitable route including oral, rectal, nasal, topical (including transdermal, buccal and sublingual), vaginal, parental (including subcutaneous, intramuscular, intravenous and intradermal) and pulmonary. It will also be appreciated that the preferred route will vary with the condition and age of the recipient and the nature of the infection.

In general, a suitable dose for each of the above-named viral infections, e.g., HCMV and HSV-1 infections, is in the range of about 0.1 to about 250 mg per kilogram body weight of the recipient per day, preferably in the range of about I to 100 mg per kilogram body weight per day and most preferably in the range of about 5 to about 20 mg per kilogram body weight per day. Unless otherwise indicated, all weights of active ingredient are calculated as the parent compound of the formula of the present invention; for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about 0.25 to about 100μM, preferably about 0.5 to about 70μM, most preferably about 1 to about 50 μM. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient.

While it is possible for the active ingredient to be administered alone, it is preferable to present it as a pharmaceutical formulation comprising at least one active ingredient, as defined above, together with one or more pharmaceutically acceptable ,carriers, such as diluents or excipients which may include, for example, fillers, extenders, wetting agents, disintegrants, surface-active agents, or lubricants, depending on the nature and mode of administration and the dosage forms. Each carrier must be "acceptable" in the sense of being compatible with the other ingredients of the formulation and not injurious to the patient. The pharmaceutical formulation may optionally include other therapeutic agents.

Formulations include 1:hose suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or nonaqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross -linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide; slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, paste, gel, spray, aerosol or oil. Alternatively, a formulation may comprise a patch or a dressing such as a bandage or adhesive plaster impregnated with active ingredients and optionally one or more excipients or diluents.

For infections of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the active ingredient may be ,employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, Le., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhances include dimethylsulfoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formation of the present invention include Tween 60, Span 80, cetostearyl alcohol, myristyl alcohol, glyceryl monostearate and sodium lauryl sulphate.

The choice of suitable oils or fats for the formation is based on achieving the desired cosmetic; properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulation in a concentration of about 0.5 to about 20% advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, a nasal spray or a nasal drops, include aqueous or oily solutions of the active ingredient.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water or injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention may include other agents conventional in the art having regard to the type of formulation in question, for example, those suitable or oral administration may include such further agents as sweeteners, thickeners and flavoring agents.

Compounds of the formula of the present may also be presented for the use in the form of veterinary formulations, which may be prepared, for example, by methods that are conventional in the art.

C. Synthesis of Compounds

1. General Synthetic Methods

The compounds of the present invention can be synthesized in accordance with the procedures described below.

FIG. 1 illustrates the synthetic route used to prepare the N-7 substituted non-nucleoside, non-phosphorylatable analogs. Compounds 3a–i were prepared from 2-amino-5-bromo-3,4-dicyanopyrrole (1) [Swayze, E. E., et al, in: L. B. Townsend and R. S. Tipson (Eds), Nucleic acid chemistry; improved and new synthetic procedures, methods and techniques, Part IV, pp. 16–18. Wiley-lnterscience, New York, 1991]. Treatment of 1 with triethylorthoformate followed by the .addition of sodium hydride and the appropriate alkylating agent gave the intermediates 2a–i which were not isolated but reacted directly with methanolic ammonia to afford the 7-substituted-4-amino-6-bromopyrrolo[ 2,3-d]pyrimidine-5-carbonitriles (3a–i). The toyocamycin analogs 4a–i were obtained from 3a–i, via catalytic hydrogenation. The thiosangivamycin analogs (5a–i) were prepared from the appropriate nitrile (4a–i) in methanolic sodium sulfide in a sealed vessel at 95° C. Similarly, reaction of the nitriles (4a–i) with methanolic sodium selenide would yield the selenoamide analogs (6a–i).

Figure 2:
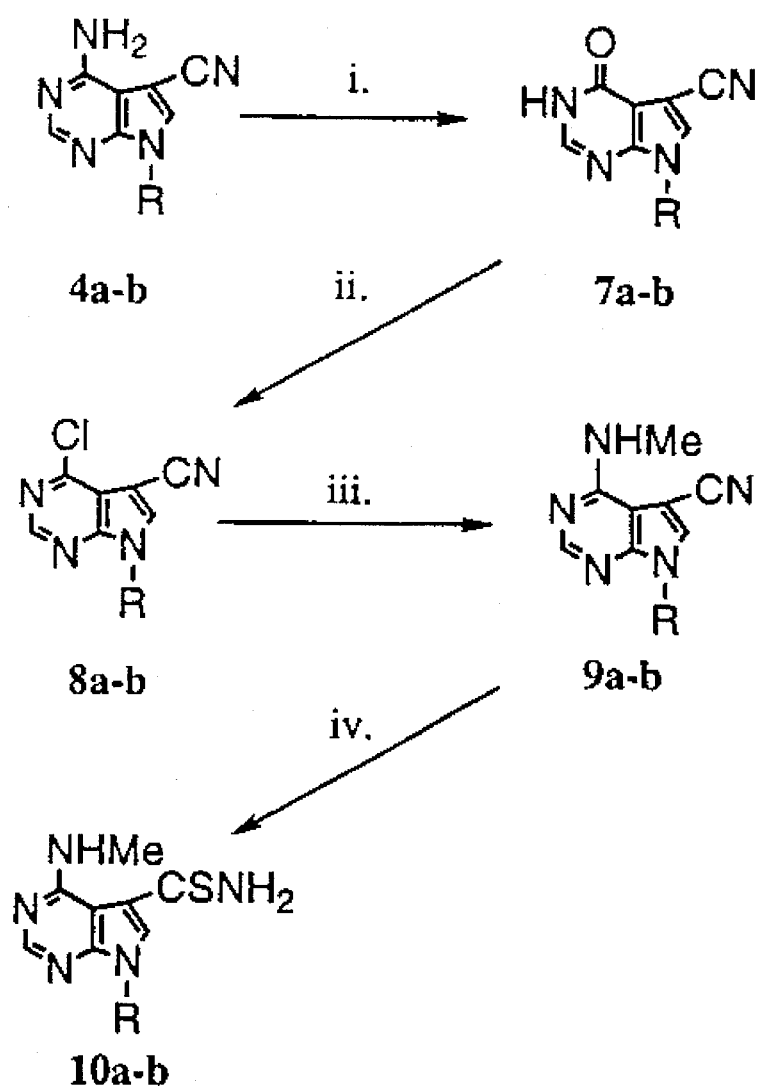
FIG. 2 is a flow chart that illustrates the synthetic route for the preparation of the C-4 modified non-nucleoside analogs (compounds 10a–b).

FIG. 2 illustrates the synthetic route used to prepare the C-4 modified non-nucleoside analogs (10a–b). Diazotization of the exocyclic amino group of compounds 4a–b was accomplished with nitrous acid to afford the 7-substituted 5-cyanopyrrolo[2,3-d]pyrimidin-4-ones, 7a–b, in good yields. Compounds 8a–b were generated in good yield by treatment of 7a–b with $POCl_3$ at reflux for ten minutes. Treatment of 8a–b with methyl amine furnished 9a–b in good yield. The nitriles (9a–b) were converted to the corresponding thioamide derivatives (10a–b).

Figure 3:
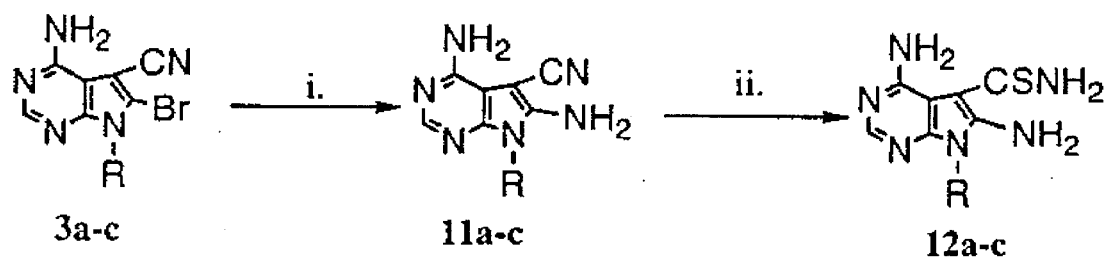
FIG. 3 is a flow chart that illustrates the synthetic route for the preparation of the 4,6-diamino substituted thioamide and nitrile analogs (compounds 11a–c, 12a–c).

FIG. 3 illustrates the synthetic route used to prepare the 4,6-diamino substituted thioamide derivatives 12a–c from the requisite nitriles, 11a–c. Compounds 1 1 a–c were synthesized in good yields by treatment of 3a–c with liquid $NH_3$ for 16h.

Melting points were taken on a Thomas-Hoover capillary melting point apparatus and are uncorrected. Thin-layer chromatography (TLC) was run on silica 60F-254 (Analtech, Inc.). Detection of components on TLC was made by UV light absorption at 254 nm. Ultraviolet spectra were recorded on a Kontron-Uvikon 860 spectrophotometer. Infrared (IR) spectra were taken on a Beckmann infrared spectrometer. Nuclear magnetic resonance (NMR) spectra were determined at 200, 300 or 360 MHz with a BRUKER WP 200/300/360 SY. The chemical shift values are expressed in δ values (parts per million) relative to the standard chemical shift of the solvent DMSO-$d_6$ unless otherwise specified. Elemental analyses were performed by M-H-W Laboratories, Phoenix, Ariz. and are within ±0.4% of the theoretical values. E. Merck silica gel (230–400 mesh) was used for gravity or flash column chromatography. Evaporations were carried out on rotary evaporator under reduced pressure (water aspirator) with the bath temperature at 40° C. unless specified otherwise. Acetonitrile and methanol was dried over activated molecular sieves (4Å).

The solvent, reagents and reaction conditions for the preparation of some representative intermediate and target compounds are presented in detail hereinafter.

2. Specific Examples of Chemical Synthesis

General Procedure for the Synthesis of 7-substituted 4-amino-6-bromopyrrolo[2,3-d]pyrimidine-5-carbonitrile Derivatives (3a–i):

3a

4-Amino-6-bromo-7-(ethoxymethyl)pyrrolo-[2,3-d]pyrimidine-5-carbonitrile (JJ 164, 3a):

A mixture of 2-amino-5-bromo-3,4-dicyanopyrrole (1, 30.0 g, 141 mmol) and freshly distilled triethylorthoformate (42.77 g, 282 mmol) in dry acetonitrile (500 mL) under argon was heated at reflux for 2.5 h, cooled to room temperature, and the solvent evaporated in vacuo. The resulting residue was coevaporated with toluene (4×50 mL) and evaporated in vacuo until a dry powder was obtained. The crude powder was dissolved in dry acetonitrile (250 mL) then treated with sodium hydride (80% w/w %, 6.36 g, 212 mmol) at room temperature. The mixture was stirred for 0.5 h, then ethoxymethyl chloride (1:3.3 g, 141 mmol) was added. The alkylation was followed closely by monitoring TLC. The reaction mixture was stirred at room temperature for 30 min, then filtered. The filtrate was evaporated and the resulting oil (2a) was transferred to a pressure bottle containing $NH_3MeOH$ (150 mL). The bottle was sealed and the solution stirred for 24 h at room temperature. The resulting suspension was cooled to 4° C. then filtered and dried overnight at 60° C. to yield 14.93 g (37%) of JJ 164. This compound was used without further purification. A sample was recrystallized from $H_2O$ in a small amount of MeOH to yield pure 3a: mp 222°–223° C.; UV/λmax nm (emM): (pH 1) 282 (19.1); (MeOH) 284 (22.1); (pH 11) 284 (19.1); $^1$H NMR (DMSO-$d_6$): a 8.23 ($^1$H, s, H-2), 7.00 (2H, br s, $NH_2$), 5.58 (2H, s, $NCH_2$), 3.46–3.52 (2H, q, $OCH_2$), 1.03–1.07 (3H, t, $CH_3$); Anal. Calc'd for $C_{10}H_{10}N_5BrO$: C, 40.56; H, 3.40; N, 23.65. Found: C, 40.70; H, 3.44; N, 23.58.

3b

4-Amino-6-bromo-7-[(2-methoxyethoxy)methyl] pyrrolo[2,3-d]pyrimidine-5-carbonitrile (JJ 194, 3b):

JJ 194 was prepared from 1 (30.0 g, 141 mmol), by the method described for 3a, to yield 13.85 g (30%) of JJ 194, 3b: mp 159°–160° C.; $^1$H NMR (DMSO-$d_6$): δ 8.23 (1H, s, H-2), 7.00 (2H, br s, $NH_2$), 5.60 (2H, s, $NCH_2$), 3.57–3.60 (2H, m, $OCH_2CH_2$) 3.36–3.39 (2H, m, $OCH_2CH_2$), 3.17 (3H, s, $OCH_3$); Anal. Calc'd for $C_{11}H_{12}N_5O_2Br$: C, 40.50; H, 3.71; N, 21.47. Found: C, 40.16; H, 3.68; N, 21.08.

3c

4-Amino-6-bromo-7-(benzyloxymethyl)pyrrolo-[2,3-d]pyrimidine-5-carbonitrile (JJ 078, 3c):

JJ 078 was prepared from I (6.0 g, 28.4 mmol), by the method described for 3a, to yield 5.4 g (54%) of JJ 078, 3c: mp 205°–208° C.; $^1$H NMR (DMSO-$d_6$): δ 8.25 (1H, s, H-2), 7.25 (5H, s, ArH), 6.99 (2H, br s, $NH_2$), 5.68 (2H, s, $NCH_2$), 4.55 (2H, s, $OCH_2$); Anal. Calc'd for $C_{15}H_{12}N_5O_2Br.H_2O$: C, 47.88; H, 3.75; N, 18.62. Found: C, 47.79; H, 3.63; N, 18.39.

3d

4-Amino-6-bromo-7-(benzyl)pyrrolo[2,3-d] pyrimidine-5-carbonitrile (LI 90, 3d):

LI 90 was prepared from I (6.0 g, 28.4 mmol), by the method described for 3a, to yield 3.98 g (43%) of LI 90, 3d: mp 259°–262° C.; $^1$H NMR (DMSO-$d_6$): δ 8.23 ($^1$H, s, H-2), 7.13–7.32 (5H, m, ArH), 7.02 (2H, br s, $NH_2$), 5.46 (2H, s, $NCH_2$); Anal. Calc'd for $C_{14}H_{10}N_5Br$: C, 51.24; H, 3.07; N, 21.34. Found: C, 51.40; H, 3.05; N, 21.38.

3e

4-Amino-6-bromo-7-(4-methylbenzyl)pyrrolo[2,3-d] pyrimidine-5-carbonitrile (LI 126, 3e):

LI 126 was prepared from I (6.0 g, 28.4 mmol), by the method described for 3a, to yield 5.0(:) g (51%) of LI 126, 3e: mp 253°–255° C.; $^1$H NMR (DMSO-$d_6$): δ 8.23 (1 Fl, s, H-2), 7.01–7.13 (4H, q, ArH), 7.00 (2H, br s, $NH_2$), 5.41 (2H, s, $NCH_2$), 2.23 (3H, s, $CH_3$); Anal. Calc'd for $C_{15}H_{12}N_5Br$: C, 52.64; H, 3.54; N, 20.47. Found: C, 52.55; H, 3.61; N, 20.38.

3f

4-Amino-6-bromo-7-(3-methylbenzyl)pyrrolo[2,3-d] pyrimidin e-5-carbonitrile (JJ 022, 3f):

JJ 022 was prepared from I (1.0 g, 4.7 mmol), by the method described for 3a, to yield 470mg (29%) of JJ 022, 3f: mp 200–201 C; $^1$H NMR (DMSO-d$_6$): δ 8.23 (1H, s, H-2), 6.85–7.22 (6H, m, ArH, NH$_2$), 5.42 (2H, s, NCH$_2$), 2.24 (3H, s, CH$_3$); Anal. Calc'd for C$_{15}$H$_{12}$N$_5$Br: C, 52.64; H, 3.54; N, 20.47. Found: C, 52.47; H, 3.46; N, 20.32.

3g

4-Amino-6-bromo-7-(2-methylbenzyl)pyrrolo[2,3-d] pyrimidine-5-carbonitrile (MC 158, 3g):

MC 158 was prepared from 1, (1.0 g, 4.7 mmol), by the method described for 3a, to yield 384 mg (24%) of MC 158, 3 g: mp> 265° C.; H $^1$H NMR (DMSO-d$_6$): δ 8.18 ($^1$H, s, H-2), 7.04 (5H, m, 3×ArH, NH$_2$), 6.26 (1H, d, ArH), 5.44 (2H, s, NCH$_2$), 2.40 (3H, s, CH$_3$); Anal. Calc'd for C$_{15}$H$_{12}$N$_5$Br: C, 52.64; H, 3.54; N, 20.47. Found: C, 52.51; H, 3.78; N, 20.28.

3h

4-Amino-6-bromo-7-(4-tert-butylbenzyl) pyrrolo[2,3-d]pyrimidine-5-carbonitrile (MC 160, 3h):

MC 160 was prepared from I (1.0 g, 4.7 mmol), by the method described for 3a, to yield 1 61 mg (9%) of MC 160, 3h: mp> 265° C.; $^1$H NMR (DMSO-d$_6$): δ8.23 (1H, s, H-2), 7.08–7.11 and 7.32–7.34 (2H each, d, 4×ArH), 6.98 (2H, br s, NH$_2$), 5.42 (2H, s, NCH$_2$), 1.22 (9H, s, CH$_3$×3); Anal. Calc'd for C$_{18}$H$_{18}$N$_5$Br: C, 56.26; H, 4.72; N, 18.23. Found: C, 56.25; H, 4.69; N, 18.00.

3i

4-Amino-6-bromo-7-(4-methoxybenzyl)pyrrolo-[2,3-d]pyrimidine-5-carbonitrile (MC 166, 3i):

MC 166 was prepared from I (1.0 g, 4.7 mmol), by the method described for 3a, to yield 614 mg (37%) of MC 166, 3i: mp 264° C. (dec); $^1$H NMR (DMSO-d$_6$): δ8.24 ($^1$H, s, H-2), 7.14–7.16 and 6.86–6.89 (2H each, d, 4×ArH), 7.00 (2H, br s, NH$_2$), 5.38 (2H, s, NCH$_2$), 3.70 (3H, s, OCH$_3$); Anal. Calc'd for C$_{15}$H$_{12}$N$_5$OBr: C, 50.29; H, 3.38; N, 19.55. Found: C, 50.40; H, 3.50; N, 19.33.

General Procedure for the Synthesis of 7-substituted 4-aminopyrrolo[2,3-d]pyrimidine-5-carbonitrile Derivatives (4a–i):

4a

4-Amino-7-(ethoxymethyl)pyrrolo[2,3-d]pyrimidine-5-carbonitrile (JJ 176, 4a):

To a mixture containing EtOAc/EtOH (600 mL, 2:1, v:v) was added 3a (14.9 g, 0.05 mol) with 1.0% Pd/C (1.49 g, 10% by weight) and 1N NaOH (50 mL, 0.05 mol). The mixture was hydrogenated at room temperature and the reaction closely monitored by TLC. After 30 min the mixture was filtered, washed with hot EtOAc (2×25 mL) and the filtrate evaporated to dryness. The resulting solid was suspended in H$_2$O/MeOH (450 mL, 3:1 v:v) and heated to boiling. To this solution was added decolorizing charcoal (1.5 g) which was filtered over Celite and the filtrate cooled overnight at 4° C. The resulting solid was collected by filtration and dried overnight at 60° C. to yield pure JJ 176, 4a (7.97 g, 73%): mp 175°–176° C.; UV λmax nm (εmM): (pH 1) 233(22.2), 272 (18.1); (MeOH) 278 (19.3); (pH 11) 277 (21.1); $^1$H NMR (DMSO-d$_6$): δ8.34 (1H, s, H-2), 8.24 ($^1$H, s, H-6), 6.87 (2H, s, NH$_2$), 5.53 (2H, s, NCH$_2$), 3.42–3.52 (2H q, CH$_2$), 1.01–108 (3H, t, CH$_3$); Anal. Calc'd for C$_{10}$H$_{11}$N$_5$O: C, 55.29; H, 5.11; N, 32.24. Found: C, 55.48; H, 5.02; N, 31.99.

4b

4-Amino-7-[(2-methoxyethoxy)methyl]pyrrolo[2,3-d]pyrimidine-5-carbonitrile (JJ 202, 4b):

JJ 202, 4b was prepared from 3b (13.85 g, 42.5 mmol), by the method described for 4a, to yield 7.85 g (75%) of JJ 202, 4b: mp 169°–171° C.; $^1$H NMR (DMSO-d$_6$): δ8.34 ($^1$H, s, H-2), 8.24 ($^1$H, s, H-6), 6.88 (2H, br s, NH$_2$), 5.56 (2H, s, NCH$_2$), 3.55–3.59 (2H, m, OCH$_2$CH$_2$), 3.36–3.39 (2H, m, OCH$_2$CH$_2$), 3.22 (3H, s, OCH$_3$); Anal. Calc'd for C$_{11}$H$_{13}$N$_5$O$_2$: C, 53.43; H, 5.30; N, 28.33. Found: C, 53.61; H, 5.37; N, 28.40.

4c

4-Amino-7-(benzyloxymethyl)pyrrolo[2,3-d]pyrimidine-5-carbonitrile (LI 240, 4c):

LI 240, 4c was prepared from 3c (2.5 g, 7.0 mmol), by the method described for 4a, to yield 1.3 g (67%) of LI 240, 4c: 170°–172° C.; $^1$H NMR (DMSO-d$_6$): δ8.37 (1H, s, H-2), 8.26 (1H, s, H-6), 7.28 (5H, s, ArH), 6.89 (2H, br s, NH$_2$), 5.65 (2H, s, NCH$_2$), 4.54 (2H, s, OCH$_2$); Anal. Calc'd for C$_{15}$H$_{13}$N$_5$O: C, 64.50; H, 4.69; N, 25.08. Found: C, 64.25; H, 4.81; N, 25.00.

4d

4-Amino-7-(benzyl)pyrrolo[2,3-d]pyrimidine-5-carbonitrile (LI 110, 4d):

LI 110, 4d was prepared from 3d (3.0 g, 9.1 mmol), by the method described for 4a, to yield LI 110, 4d (1.28 g, 56%) as a white solid. A small sample was recrystallized from MeOH: mp 218°–219° C.; $^1$H NMR (DMSO-d$_6$): δ8.31 ($^1$H, s, H-2), 8.22 ($^1$H, s, H-6), 7.25–7.32 (5H, m, ArH), 6.80 (2H, br s NH$_2$), 5.39 (2H, s, NCH$_2$); Anal. Calc'd for C$_{14}$H$_{11}$N$_5$: C, 67.45; H, 4.45; N, 28.10. Found: C, 67.50; H, 4.41; N, 28.23.

4e

4-Amino-7-(4-methylbenzyl)pyrrolo[2,3-d]pyrimidine-5-carbonitrile (LI 130, 4e):

LI 130, 4e was prepared from 3e (400 mg, 1.2 mmol), by the method described for 4a, to yield 249 mg (81%) of LI 130, 4e: mp 244°–245° C.; $^1$H NMR (DMSO-d$_6$): δ8.29 ($^1$H, s, H-2), 8.22 ($^1$H, s, H-6), 7.11–7.18 (4H, q, ArH), 6.82 (2H, br s, NH$_2$), 5.33 (2H, s, NCH$_2$), 2.24 (3H, s, CH$_3$); Anal. Calc'd for C$_{15}$H$_{13}$N$_5$: C, 68.40; H, 498; N, 26.60. Found: C, 68.40; H, 5.00; N, 26.74.

4f

4-Amino-7-(3-methylbenzyl)pyrrolo[2,3-d]pyrimidine-5-carbonitrile (MC 168, 4f):

MC 168, 4f was prepared from 3f (400 rag, 1.1 mmol), by the method described for 4a, to yield 200 mg (69%) of MC 168, 4f: mp 238°–239° C.; $^1$H NMR (DMSO-d$_6$): δ8.30 ($^1$H, s, H-2), 8.26 ($^1$H, s, H-6), 7.03–7.22 (4H, m, ArH), 6.85 (2H, br s, NH$_2$), 5.34 (2H, s, NCH$_2$), 2.24 (3H, s, CH$_3$); Anal. Calc'd for C$_{15}$H$_{13}$N$_5$: C, 68.42; H, 4.98; N, 26.60. Found: C, 68.28; H, 5.06; N, 26.40.

4g

4-Amino-7-(2-methylbenzyl)pyrrolo[2,3-d]pyrimidine-5-carbonitrile (LI 246, 4g):

LI 246, 4g was prepared from 3g (250 mg, 0.73 mmol), by the method described for 4a, to yield 80 mg (41%) of LI 246, 4g: mp 256°–259° C.; $^1$H NMR (DMSO-d$_6$): δ8.21 ($^1$H, s, H-2), 8.16 ($^1$H, s, H-6), 7.15–7.19 (3H, m, 3×ArH), 6.86 (2H, br s, NH$_2$, D$_2$O exchangeable), 6.78–6.76 (1H, d, ArH), 5.39 (2H, s, NCH$_2$), 2.32 (3H, s, CH$_3$); Anal. Calc'd for C$_{15}$H$_{13}$N$_5$. 0.5H$_2$O: C, 66.16; H, 5.18; N, 25.72. Found: C, 66.06; H, 5.01; N, 25.68.

4h

4-Amino-7-(4-tert-butylbenzyl)pyrrolo[2,3-d]pyrimidine-5-carbonitrile (JJ 104, 4h):

JJ 104, 4h was prepared from 3h (4.4 g, 11.5 mmol), by the method described for 4a, to yield 780 mg (22%) of JJ 104, 4h: mp 242°–245° C.; $^1$H NMR (DMSO-d$_6$): δ8.32 (1H, s, H-2), 8.23 (1H, s, H-6), 7.40–7.33 and 7.21–7.15 (2H each, d, 4×ArH), 6.85 (2H, s, NH$_2$), 5.34 (2H, s, NCH$_2$), 1.22 (9H, s, CH$_3$×3); Anal. Calc'd for C$_{18}$H$_{19}$N$_5$: C, 70.79; H, 6.27; N, 22.94. Found: C, 70.82; H, 6.49; N, 22.76.

4i

4-Amino-7-(4-methoxybenzyl)pyrrolo[2,3-d]pyrimidine-5-carbonitrile (JJ 092, 4i):

JJ 092, 4i was prepared from 3i (4.0 g, 11.2 mmol), by the method described for 4a, to yield 638 mg (20%) of JJ 092, 4i: mp 220°–221° C.; $^1$H NMR (DMSO-d$_6$): δ8.29 (1H, s, H-2), 8.22 (1H, s, H-6), 7.26–7.24 and 6.89–6.87 (2H each, d, 4×ArH), 6.86 (2H, br s, NH$_2$), 5.30 (2H, s, NCH$_2$), 3.70 (3H, s, OCH$_3$); Anal. Calc'd for C$_{15}$H$_{13}$N$_5$O: C, 64.50; H, 4.69; N, 25.08. Found: C, 64.68; H, .4.70; N, 24.82.

General Procedure for the Synthesis of 7-substituted 4-aminopyrrolo[2,3-d]pyrimidine-5-thiocarboxamide Derivatives (5a–i):

5a

4-Amino-7-(ethoxymethyl)pyrrolo[2,3-d]pyrimidine-5-thiocarboxamide (LI 216, 5a):

Dry H$_2$S was passed through a solution of sodium methoxide (97 mg, 1.8 mmol) in dry methanol (20 mL) for 0.5 h. The nitrile 4a (200 mg, 0.9 mmol) was added in one portion, and the mixture was stirred in a sealed pressure tube at 95° for 2 h. The resulting solution was allowed to cool to room temperature, then adjusted to pH 7 with 1N HCl. The solvent was rotary evaporated to dryness and the resulting compound was recrystallized from H$_2$O containing a small amount of EtOH to yield 210 mg (93%) of LI 216, 5a: mp 207°–209° C.; $^1$H NMR (DMSO-d$_6$): δ9.46 and 9.65 (1H each, s, CSNH$_2$), 8.14($^1$H, s, H-2), 7.92 (2H, brs, NH$_2$), 7.85 ($^1$H, s, H-6), 5.51 (2H, s, NCH$_2$), 3.46–3.52 (2H, q, OCH$_2$), 1.05–1.09 (3H, t, CH$_3$); Anal. Calc'd for C$_{10}$H$_{13}$N$_5$OS.0.3H$_2$O: C, 46.78; H, 5.22; N, 27.28. Found: C, 47.08; H 5.39; N, 26.92.

5b

4-Amino-7-[(2-methoxyethoxy)methyl]pyrrolo[2,3-d]pyrimidine-5-thiocarboxamide (JJ 048, 5b):

JJ 048, 5b was prepared from 4b (600rag, 2.4 retool), by the method described for 5a, to yield 431 mg (64%) of JJ 048, 5b: mp 150°–152° C.; $^1$H NMR (DMSO-d$_6$): δ9.62 and 9.47 (1H each, s, CSNH$_2$), 8.14 (1H, s, H-2), 7.92 (2H, br s, NH$_2$), 7.85 ($^1$H, s, H-6), 5.53 (2H, s, NCH$_2$), 3.57–3.60 (2H, m, OCH$_2$CH$_2$), 3.38–3.41 (2H, m, OCH$_2$CH$_2$), 3.19 (3H, s, OCH$_3$); Anal. Calc'd for C$_{11}$H$_{15}$N$_5$O$_2$S: C, 46.96; H, 5.37; N, 24.90. Found: C, 46.81; H, 5.36; N, 24.88.

5c

4-amino-7-(benzyloxymethyl)pyrrolo[2,3-d]pyrimidine-5-thiocarboxamide (LI 250, 5c):

LI 250, 5c was prepared from 4c (200 mg, 0.7 retool), by the method described for 5a, to yield 179 mg (80%) LI 250, 5c: mp 180°–182° C.; $^1$H NMR (DMSO-d$_6$): δ9.55 and 9.52 (1H each, s, CSNH$_2$), 8.17 ($^1$H, s, H-2), 7.93 (2H, br s, NH$_2$), 7.91 (1H, s, H-6), 7.26–7.34 (5H, m, ArH), 5.63 (2H, s, NCH$_2$), 4.55 (2H, s, OCH$_2$); Anal. Calc'd for C$_{15}$H$_{15}$N$_5$OS: C, 57.49; H, 4.82; N, 22.35. Found: C, 57.43; H, 4.74; N, 22.09.

5d

4-Amino-7-(benzyl)pyrrolo[2,3-d]pyrimidine-5-thiocarboxamide(LI 128, 5d):

LI 128, 5d was prepared from 4d (250 rag, 1 retool), by the method described for 5a, to yield 222 mg (78%) of LI 128, 5d: mp 192°–195° C.; $^1$H NMR (DMSO-d$_6$): δ9.51 and 9.37 (1H each, s, CSNH$_2$), 8.13 (1H, s, H-2), 7.93 (2H, br s, NH$_2$), 7.86 ($^1$H, s, H-6), 7.25–7.34 (5H, m, ArH), 5.35 (2H, s, NCH$_2$); Anal. Calc'd for C$_{14}$H$_{13}$N$_5$S: C, 59.34; H, 4.62; N, 24.72. Found: C, 59.39; H, 4.82; N, 24.81.

5e

4-Amino-7-(4-methylbenzyl) pyrrolo[2,3-d]pyrimidine-5-thiocarboxamide (LI 144, 5e):

LI144, 5e was prepared from 4e (200 mg, 0.8 mmol), by the method described for 5a, to yield 207mg (87%) of L1144, 5e as a yellow solid: mp 225°–227° C.; $^1$H NMR (DMSO-d$_6$): δ9.51 and 9.37 ($^1$H each, s, CSNH$_2$), 8.13 ($^1$H, s, H-2), 7.95 (2H, br s, NH$_2$), 7.83 ($^1$H, s, H-6), 7.11–7.20 (4H, m ArH), 5.29 (2H, s, NCH$_2$), 2.24 (3H, s, CH$_3$); Anal. Calc'd for C$_{15}$H$_{15}$N$_5$S: C, 60.58; H, 5.08; N, 23.55. Found: C, 60.36; H, 5.27; N, 23.55.

5f

4-Amino-7-(3-methylbenzyl)pyrrolo[2,3-d]pyrimidine-5-thiocarboxamide (JJ 072. 5f):

JJ 072 was prepared from 4f (400 mg, 1.5 mmol), by the method described for 5a, to yield 313 mg (70%) of JJ 072, 5f: mp 225°–226° C.; $^1$H NMR (DMSO-$d_6$): δ9.55 and 9.38 (1H each, s, CSNH$_2$), 8.14 (1H, s, H-2), 7.95 (2H, br s, NH$_2$), 7.85 (1H, s, H-6), 7.19–7.25 (1H, t, ArH), 7.06–7.12 (3H, m, ArH), 5.31 (2H, s, NCH$_2$), 2.26 (3H, s, CH$_3$); Anal. Calc'd for $C_{15}H_{15}N_5S$, 0.5H$_2$O: C, 58.80; H, 5.26; N, 22.86. Found: C, 58.41; H, 5.37; N, 22.63.

5g

4-Amino-7-(2-methylbenzyl)pyrrolo[2,3-d]pyrimidine-5-thiocarboxamide (JJ 026, 5g):

JJ 026, 5g was prepared from 4g (300 mg, 1.1 mmol), by the method described for 5a, to yield 287 mg (88%) of JJ 026, 5g: mp 248°–250° C.; 1H NMR (DMSO-$d_6$): δ9.50.and 9.37 ($^1$H each, s, CSNH$_2$), 8.13 (1H, s, H-2), 7.99 (2H, br s, NH:2), 7.72 (1H, s, H-6), 7.12–7.20 (3H, m, 3×ArH), 6.78–6.85 ($^1$H, d, ArH), 5.34 (2H, s, NCH$_2$), 2.32 (3H, s, CH$_3$); Anal. Calc'd for $C_{15}H_{15}N_5S$: C, 60.58; H, 5.08; N, 23.55. Found: C, 60.66; H, 5.10; N, 23.48.

5h

4-Amino-7-(4-tert-butylbenzyl)pyrrolo[2,3-d]pyrimidine-5-thiocarboxamide (JJ 114, 5h):

JJ 114 was prepared from 4h (400 mg, 1.4 mmol), by the method described for 5a, to yield 250 mg (53%) of JJ 114, 5h: mp 145°–147° C.; $^1$H NMR (DMSO-$d_6$): δ9.50 and 9.36 (1H each, s, CSNH$_2$), 8.13 (1H, s, H-2), 7.93 (2H, s, NH$_2$), 7.85 (1H, s, H-6), 7.35–7.32 and 7.23–7.20 (4H, m, ArH), 5.30 (2H, s, NCH$_2$), 1.22 (9H, s, CH$_3$×3); Anal. Calc'd for $C_{18}H_{21}N_5S$: C, 63.69; H, 6.24; N, 2.0.63. Found: C, 63.81; H, 6.16; N, 20.45.

5i

4-Amino-7-(4-methoxybenzyl)pyrrolo[2,3-d]pyrimidine-5-thiocarboxamide (JJ 098, 5i):

JJ 098, 5i was prepared from 4i (388mg, 1.4 mmol), by the method described for 5a, to yield 277mg (63%) of JJ 096, 5i: mp 222°–224° C.; $^1$H NMR (DMSO-$d_6$): δ9.49 and 9.35 (1H each, s, CSNH$_2$), 8.13 (1H, s, H-2), 7.92 (2H, br s, NH$_2$), 7.82 (1H, s, H-6), 7.27–7.25 and 6.89–6.86 (2H each, d, 4×ArH), 5.25 (2H, s, NCH$_2$), 3.70 (3H, s, OCH$_3$); Anal. Calc'd for $C_{15}H_{13}N_5S \cdot 0.5H_2O$: C, 55.88; H, 5.00; N, 21.73. Found: C, 56.06; H, 5.08; N, 21.72.

General Procedure for the Synthesis of 7-substituted 4-aminopyrrolo[2,3-d]pyrimidine-5-selenocarboxamide Derivatives (6a–i):

6a

4-Amino-7-(ethoxymethyl)pyrrolo[2,3-d]pyrimidine-5-selenocarboxamide (6a):

Dry H$_2$Se is passed through a solution of sodium methoxide (46 mg, 0.86 mmol) in dry methanol (25 mL) for 0.5 h. The nitrile 4a (100 mg, 0.43 retool) is added in one portion, and the mixture stirred in a sealed pressure tube at 95° for 2 h. The resulting solution is allowed to cool to room temperature, then adjusted to pH 7 with 1N HCl. The solvent is rotary evaporated to dryness and the resulting compound recrystallized from H$_2$O containing a small amount of EtOH to yield the selenocarboxamide 6a.

6b–i

The selenocarboxamide analogs 6b–i are obtained from the nitriles 4b-i using the method described for 6a.

7a

5-Cyano-7-(ethoxymethyl)pyrrolo[2,3-d]pyrimidin-4-one (JJ 178, 7a):

JJ 176, 4a (7.97 g, 36.7 mmol) was suspended in distilled H$_2$O (414 mL) and AcOH (36 mL). This suspension was heated to 50° C. and NaNO$_2$ (17.73 g, 256.9 mmol) was added in six batches over a period of 4.5 h.

Following the additions of NaNO$_2$, the reaction was heated to 70° C. for 16 h. The resulting solid was cooled to 4° C. for 24 h, collected by filtration and dried in vacuo at 60° C. overnight to yield 7.21 g (90%) of pure JJ 178, 7a: mp 209°–211° C.; IR (KBr) u 2220 (CN), 1670 (C =0), 1590 (NH) cm$^{-1}$; UV λmax nm (εmM): (pH 1)).64 (12.5); (MeOH) 263 (12.5); (pH 11) 274 (13.0); $^1$H NMR (DMSO-$d_6$): δ12.5 ($^1$H, br s, NH, D$_2$O exchangeable), 8.23 (1H, s, H-2), 8.09 (1H, s, H-6), 5.50 (2H, s, NCH$_2$), 3.42–3.52 (2H, q, CH$_2$), 1.02–1.09 (3H, t, CH$_3$); Anal. Calc'd for $C_{10}H_{10}N_4O_2$: C, 55.04; H, 4.62; N, 25.45. Found: C, 54.83; H, 4.76; N, 25.45.

7b

5-Cyano-7-[(2-methoxyethoxy)methyl]pyrrolo[2,3-d]pyrimidin-4-one (JJ 192, 7b):

JJ 192, 7b was prepared from 4b (300 mg, 1.2 mmol), by the method described for 7a, to yield 217 mg (73%) of JJ 192, 7b: $^1$H NMR (DMSO-$d_6$): δ 12.5 ($^1$H, br s, NH), 8.22 ($^1$H, s, H-2), 8.09 ($^1$H, s, H-6), 5.53 (2H, s, NCH$_2$), 3.56–3.58(2H, m, OCH$_2$CH$_2$), 3.37–3.39 (2H, m, OCH$_2$CH$_2$), 3.18 (3H, s, OCH$_3$); Anal. Calc'd for $C_{11}H_{12}N_4O_3$: C, 53.22; H, 4.87; N, 22.57. Found: C, 53.00; H, 5.05; N, 22.59.

8a

4-Chloro-7-(ethoxymethyl)pyrrolo [2,3-d] pyrimidine-5-carbonitrile (JJ 172, 8a):

7a (1.14 g, 5.2 mmol) was dissolved in POCl$_3$ (10 mL) and the solution was heated at reflux for 12 min. The hot solution was poured onto ice water (100 mL), and the pH of the resulting mixture adjusted to 7 with NH$_4$OH (38%, 5 mL). The solution was extracted with CH$_2$Cl$_2$ (2×75 mL) from distilled H$_2$O (300 mL total) and NaHCO$_3$ (1×5 mL). The organic layer was collected and dried over MgSO$_4$, filtered and the filtrate evaporated to dryness to furnish a yellow solid (987 mg, 80%). A small sample (50 mg) was recrystallized from a MeOH/H$_2$O mixture and decolorizing charcoal to furnish 8a as a pure white powder: mp 125°–126° C.; IR (KBr) u 2210 (CN), 1100 (C-Cl) cm$^{-1}$; UV λmax nm (εmM): (pH 1) 274 (7.7); (MeOH) 274 (8.1); (pH 11) 274 (14.0); $^1$H NMR (DMSO-$d_6$): δ8.87 and 8.88 (1H each, s, H-2 and H-6), 5.68 (2H, s, NCH$_2$), 3.60–3.45 (2H, q, CH$_2$), 1.04–1.09 (3H, t, CH$_3$); Anal. Calc'd for $C_{10}H_9N_4OCl$: C, 50.75; H, 3.83; N, 23.68. Found: C, 50.70; H, 4.00; N, 23.51.

8b

4-Chloro-7-[(2-methoxyethoxy)methyl]pyrrolo-[2,3-d]pyrimidine-5-carbonitrile (JJ 242, 8b):

JJ 242, 8b was prepared from 7b (5.34 g, 21.5 mmol) by the method described for 8a, to yield 3.64 g (63%) of 8b as a white powder: mp 105°–106° C. (dec); $^1$H NMR (DMSO-$d_6$): δ8.87 and 8.86 ($^1$H each, s, H-2 and H-6), 5.71 (2H, s, NCH$_2$), 3.59–3.63 (2H, m, OCH$_2$CH$_2$), 3.36–3.39 (2H, m, OCH$_2$CH$_2$), 3.16 (3H, s, OCH$_3$); Anal. Calc'd for C$_{11}$H$_{11}$N$_4$O$_2$Cl: C, 49.54; H, 4.16; N, 21.01. Found: C, 49.39; H, 4.31; N, 21.08.

9a

4-Methylamino-7-(ethoxymethyl)pyrrolo[2,3-d]pyrimidine-5-carbonitrile (JJ 278, 9a):

8a (800 mg, 3.4 mmol) was dissolved in methylamine (100 mL, 33% in abs. EtOH) and the solution stirred at room temperature for 2.5 h. The solution was then allowed to stand at 4° C. for 16 hr and the solid collected by filtration to furnish 548 mg (70%) of JJ 278, 9a as a pure white powder: mp 175°–177° C.; UV λmax nm (ε mM): (pH 1) 275 (19.8), 235 (17.4); (MeOH) 281 (21.0); ,[pH 11) 282 (20.4), 234 (10.3); $^1$H NMR (DMSO-$d_6$): δ 8.33 and 8.32 , [1H each, s, H-2 and H-6), 6.73–6.74 (1H, q, NH), 5.33(2H, s, NCH$_2$), 3.43–3.49 (2H, q, CH$_2$), 2.98–3.00 (3H, d, CH$_3$), 1.01–1.06 (3H, t, CH$_3$); Anal. Calc'd for C$_{11}$H$_{13}$N$_5$O: C, 57.13; H, 5.66; N, 30.29. Found: C, 57.20; H, 5.75; N, 30.27.

9b

4-Methylamino-7-[(2-methoxyethoxy)methyl]pyrrolo[2,3-d]pyrimidine-5-carbonitrile (MC 014, 9b):

MC 014, 9b was prepared from 8b (800 mg, 3.0 mmol), by the method described for 9a, to yield 600 mg (77%) of MC 014, 9b: mp 134°–135° C.; $^1$H NMR (DMSO-$d_6$): δ8.33 and 8.32 ($^1$H each, s, H-2 and H-6), 6.73–6.76 ($^1$H, q, NH), 5.56 (2H, s, NCH$_2$), 3.55–3.58 (2H, m, OCH$_2$CH$_2$), 3.36–3.39 (2H, m, OCH$_2$CH$_2$), 3.17 (3H, s, OCH$_3$), 2.98–3.00 (3H, d, CH$_3$); Anal. Calc'd for C$_{12}$H$_{15}$N$_5$O$_2$: C, 55.16; H, 5.79; N, 26.81. Found: C, 55.08; H, 5.88; N, 27.00.

10a

4-Methylamino-7-(ethoxymethyl)pyrrolo[2,3-d]pyrimidine-5-thiocarboxamide (MC 032, 10a):

NaOMe (47 mg, 0.8 mmol) in dry MeOH (75 mL) was saturated with H$_2$S (g) for 30 min. This solution was transferred to a steel vessel containing 9a (100 mg, 0.4 mmol). The vessel was sealed and heated at 100° C. in an oil bath for 24 h. The solution was allowed to cool to room temperature and the pH adjusted to 7 with 1N HCl (2 mL). To this solution was added 1.2 g silica which was applied to a column prepacked with silica. The column was eluted with hexanes/EtOAc (70:30, v:v) to afford 10a. The compound was recrystallized from a H$_{20}$/EtOH mixture to yield 100 mg (94%) of MC 032, 10a: mp 157°–158° C.; UV λmax nm (εmM): (pH 1) 249 (17.4); (MeOH) 286 (15.9); ,[pH 11) 281 (16.7); $^1$H NMR (DMSO-$d_6$): δ9.49 and 9.65 ($^1$H each, br s, CSNH$_2$), 9.11–9.15 ($^1$H, q, NH), 8.24 (1H, s, H-2), 7.87 ($^1$H, s, H-6), 5.52 (2H, s, NCH$_2$), 3.46–3.52 (2H, q, CH$_2$), 2.98–3.01 (3H, d, NCH$_3$), 1.04–1.08 (3H, t, CH$_3$); Anal. Calc'd for C$_{11}$H$_{15}$N$_5$OS: C, 49.79; H, 5.70; N, 26.40. Found: C, 49.69; H, 5.94; N, 26.20.

10b

4-Methylamino-7-[(2-methoxyethoxy)methyl]pyrrolo[2,3-d]pyrimidine-5-thiocarboxamide (MC 030, 10b):

10b was prepared from 9b (100 mg, 0.4 mmol), by the method described for 10a, to yield 75 mg (64%) of MC 030, 10b: mp 139°–141 ° C.; 1H NMR (DMSO-$d_6$): δ9.65 and 9.50 (1H each, br s, CSNH$_2$), 9.12–9.13 (1H, q, NH), 8.24 ($^1$H, s, H-2), 7.87 ($^1$H, s, H-6), 5.55 (2H, s, NCH$_2$), 3.57–3.60 (2H, m, OCH$_2$CH$_2$), 3.38–3.41 (2H, m, OCH$_2$CH$_2$), 3.19 (3H, s, OCH$_3$), 2.97–2.98 (3H, d, NCH$_3$); Anal. Calc'd for C$_{12}$H$_{17}$N$_5$O$_2$S: C, 48.79; H, 5.86; N, 23.93. Found: C, 48.69; H, 5.86; N, 23.93.

11a

4,6-Diamino-7-(ethoxymethyl)pyrrolo[2,3-d]pyrimidine-5-carbonitrile (JJ 028, 11a):

A 125 mL steel vessel containing 3a (2.5 g) was charged with 75 mL of NH$_3$ (I). The vessel was sealed and the reaction was heated at 100° C. for 16 h. The vessel was allowed to cool to room temperature and further cooled to −75° C. at which time the vessel was vented. The resulting solid was suspended in H$_2$O and heated to boiling. Following filtration, the filtrate was allowed to stand at 4° C. for 16 hr and pure JJ 028, 11a was collected by filtration(1.70 g, 87%): mp 229°–230° C.; UV λmax nm(εmM): (pH 1) 293 (15.9); (MeOH).295 (16.0); (pH 11) 290 (19.9); $^1$H NMR (DMSO-$d_6$): δ8.00 (1H, s, H-2), 7.22 (2H, br s, NH$_2$, D$_2$O exchangeable), 6.10 (2H, br s, NH$_2$, D$_2$O exchangeable), 5.42 (2H, s, NCH$_2$), 3.44–3.48 (2H, q, CH$_2$), 1.03–1.07 (3H, t, CH$_3$); Anal. Calc'd for C$_{10}$H$_{12}$N$_6$O: C, 51.71; H, 5.21; N, 36.19. Found: C, 51.81; H, 5.44; N, 36.30.

11b

4,6-Diamino-7-[(2-methoxyethoxy)methyl]pyrrolo-[2,3-d]pyrimidine-5-carbonitrile (JJ 070, 11b):

JJ 070, 11b was prepared from 3b (670 mg, 2.1 mmol), by the method described for 11a, to furnish ,JJ 070, 11b in 74% yield (396 mg): mp 190–192 C; H NMR (DMSO-$d_6$): δ8.00 (1H, s, H-2), 7.25 (2H, br s, NH$_2$), 6.13 (2H, br s, NH$_2$), 5.44 (2H, s, NCH$_2$), 3.34–3.55 (2H, m, OCH$_2$CH$_2$), 3.37–3.39 (2H, m, OCH$_2$CH$_2$), 3.19 (3H, s, OCH$_3$); Anal. Calc'd for C$_{11}$H$_{14}$N$_6$O$_2$: C, 50.37; H, 5.38; N, 32.05. Found: C, 50.37; H, 5.34; N, 31.90.

11c

4,6-Diamino-7-(benzyloxymethyl)pyrrolo[2,3-d]pyrimidine-5-carbonitrile (JJ 082, 11c):

JJ 082, 11c was prepared from 3c (1.0 g, 2.8 mmol), by the method described for 11a, to yield 695 mg (84%) of 11c as a white solid after recrystallization from a water and methanol mixture containing decolorizing charcoal: mp 218°–219° C.; $^1$H NMR (DMSO-$d_6$): δ8.04 (1H, s, C-2), 7.29 (7H, m, ArH and NH$_2$), 6.13 (2H, br s, NH$_2$), 5.55 (2H, s, NCH$_2$), 4.52 (2H, s, OCH$_2$); Anal. Calc'd for C$_{15}$H$_{14}$N$_6$O: C, 61.21; N, 4.79; H, 28.56. Found: C, 61.20; H, 4.98; N, 28.50.

12a

4,6-Diamino-7-(ethoxymethyl)pyrrolo[2,3-d]pyrimidine-5-thiocarboxamide (JJ 076, 12a):

NaOMe (194 mg, 3.6 mmol)in dry MeOH (60 mL) was saturated with $H_2S$ (g) for 30 min. This solution was transferred to a steel vessel containing JJ 038 (1 la, 400 rag, 1.8 mmol). The vessel was sealed and heated at 100° C. in an oil bath for 19 hr. The solution was allowed to cool to room temperature and the pH of the solution was adjusted to 7 with 1N HCl (2.5 mL). The resulting solution was evaporated to dryness and the solid recrystallized from $H_2O$/MeOH and decolorizing charcoal to furnish pure JJ 076, 12a (204 mg, 43%): mp 209°–210° C.; UV λmax nm (ϵmM): (pH 1) 366 (13.6), 277 (15.5); (MeOH) 364 (11.7), 279 (14.6); (pH 11) 360 (12.3), 269 (17.4); $^1H$ NMR (DMSO-$d_6$): δ8.15 and 8.02 (2H each, br s, 4-$NH_2$ and $CSNH_2$, $D_2O$ exchangeable), 8.06 (1H, s, H-2), 6.39 (2H, br s, $NH_2$, D20 exchangeable), 5.49 (2H, s, $CH_2$), 3.45–3.52 (2H, q, $CH_2$), 1.06–1.10 (3H, t, $CH_3$); Anal. Calc'd for $C_{10}H_{14}N_6OS$: C, 45.10H, 5.30; N, 31.56. Found: C, 45.13; H, 5.30; N, 31.57.

12b

4,6-Diamino-7-[(2-methoxyethoxy)methyl]pyrrolo-[2,3-d]pyrimidine-5-thiocarboxamide (JJ 088, 12b):

JJ 088, 12b was prepared from 1113 (396 mg,l.5 mmol), by the method described for 12a, to furnish JJ 088, 12b in 61% yield (269 mg): mp 199–200 C; $^1H$ NMR (DMSO-$d_6$): δ8.16 (2H, br s, $CSNH_2$), 8.07 (1H, s, H-2), 8.04 (2H, br s, $NH_2$), 6.41 (2H, br s, $NH_2$), 5.52 (2H, s, $NCH_2$), 3.57–3.60 (2H, m, $OCH_2CH_2$), 3.40–3.43 (2H, m, $OCH_2CH_2$), 3.21 (3H, s, $OCH_3$); Anal. Calc'd for $C_{11}H_{16}N_6O_2S$: C, 44.58; H, 5.44; N, 28.36. Found: C, 44.43; H, 5.38; N, 28.18.

12c

4,6-Diamino-7-(benzyloxymethyl)pyrrolo[2,3-d] pyrimidine-5-thiocarboxamide (JJ 100, 12c ):

JJ 100, 12c was prepared from 11c (418 mg, 1.4 mmol), by the method described for 12a0 to yield 194 mg (42%) of 12c after recrystallization from a mixture of water and methanol: mp 199°–200° C.; $^1H$ NMR (DMSO-$d_6$): δ8.17 (2H, br s, $CSNH_2$, $D_2O$ exchangeable), 8.09–8.08 (3H, m, H-2 and $NH_2$, 2H D20 exchangeable), 7.31 (5H, m, ArH), 6.42 (2H, br s, $NH_2$, D20 exchangeable), 5.61 (2H, s, $NCH_2$), 4.54 (2H, s, $OCH_2$); Anal. Calc'd for $C_{15}H_{16}N_6OS$: C, 54.86; N, 4.91; H, 25.59. Found: C, 54.90; H, 5.08; N, 25.36.

D. Examples of Testing and Use of Compounds

1. In Vitro Antiviral Evaluation Methods

(a) Cells and viruses.

The routine growth and passage of KB and BSC-1 cells was performed in monolayer cultures using minimal essential medium (MEM) with either Hanks salts [MEM(H) ] or Earle salts [MEM(E)] supplemented with 10% calf serum. The sodium bicarbonate concentration was varied to meet the buffering capacity required. ,Cultures of diploid human foreskin fibroblast (HFF) or MRC-5 cells were grown in medium consisting of MEM(E) with 10% fetal bovine serum. Cells were passaged at 1:2 to 1:10 dilutions according to conventional procedures by using 0.05% trypsin plus 0.02% EDTA in a HEPES buffered salt solution (HBS) [Shipman, C., Jr., *Proc. Soc. Exp. Biol.*, 130:305–310, 1969] as described previously [Turk, S. R., et. al, *Antimicrob. Agents Chemother.*, 31:544–550, 1987]. HFF and MRC-5 cells were passaged only at 1:2 dilutions. The Towne strain, plaque-purified isolate $P_o$, of HCMV was kindly provided by Dr. Mark Stinski, University of Iowa. The KOS strain of HSV-1 was used in most experiments and was provided by Dr. Sandra K. Weller, University of Conn.

(b) Virological procedures.

Stock HCMV was prepared by infecting HFF cells at a multiplicity of infection (m.o.i.) of <0.01 plaque-forming units (p.f.u.) per cell. Cell growth medium was changed every four days until cytopathology was evident in all cells (approximately 21 days). Supernatant fluids were retained as the virus stock.

High titer HSV-1 stocks were prepared by infecting BSC cells at an m.o.i. of < 0.1 as detailed previously [Turk, S. R., et al., *Antimicrob. Agents Chemother.*, 31:544–550, 1987].

Virus titers were determined using monolayer cultures of HFF cells for HCMV and monolayer cultures of BSC-1 cells for HSV-1 as described earlier [Prichard, M. N., et al., *J. Virol. Methods*, 28:101–106, 1990]. Briefly, HFF or BSC-1 cells were planted as described above in 96-well cluster dishes and incubated overnight at 37° C. in a humidified 3% $CO_2$ - 97% air atmosphere. The next day cultures were inoculated with HCMV or HSV-1 and serially diluted 1:3 across the remaining eleven columns of the 96-well plate. Cultures were incubated at 37° C. for 2 hr to permit virus adsorption and then virus inoculum was replaced with 0.2 ml of fresh medium. Cultures were incubated for seven days for HCMV, two or three days for HSV-1, the medium was removed, and the cell sheets were stained with 0.1% crystal violet in 20% methanol.

HCMV plaques were enumerated under 20-fold magnification in wells having the dilution which gave 5 to 20 plaques per well. HSV-1 plaques were counted with the unaided eye or at 3–10 fold magnification. Virus titers were calculated according to the following formula: Titer (p.f.u./ml) = number of plaques×5×$3^n$; where n represents the nth dilution of the virus used to infect the well in which plaques were enumerated.

(c) Assays for Antiviral Activity.

The effect of compounds on the replication of HCMV has been measured using a plaque reduction assay. HFF cells in 24-well cluster dishes were infected with approximately 100 p.f.u. of HCMV per $cm^2$ cell sheet using the procedures detailed above. Following virus adsorption, compounds dissolved in growth medium were added to duplicate wells in three to six selected concentrations. Following incubation at 37° C. for 7 to 10 days, cell sheets were fixed, stained with crystal violet and microscopic plaques enumerated as described above.

Drug effects were calculated as a percentage of reduction in number of plaques in the presence of each drug concentration compared to the number observed in the absence of drug. Ganciclovir (DHPG) was used as a positive control in all experiments.

Plaque reduction experiments with HSV-1 were performed using monolayer cultures of BSC-1 cells. The assay was performed exactly as described above except that the 0.2 ml virus suspension contained approximately 100 p.f.u. of HSV-1. Compounds to be tested were dissolved in the overlay medium at concentrations usually ranging from 0.1 to 100 µM in half- or one-logarithm$_{10}$ dilutions.

An ELISA also was employed to detect HSV-1. 96-well cluster dishes were planted with BSC-1 cells at 10,000 cells per well, in a total volume of 200 µM per well of MEM(E) plus 10% calf serum. After overnight incubation at 37° C., drug and HSV-1 was added at a concentration of 100 PFU/well. ELISA plates were blocked with 200 µl per well of 10% calf serum and 0.05% tween in HBS. After incubation for 30 minutes, the blocking agent was rinsed two times with HBS-T. A 1:400 dilution of AP conjugated rabbit anti-HSV- 1 antibody in HBS-F was added. Plates were sealed with adhesive sheet, and incubated on rocker for one hour at 37° C. Plates were developed in the dark with 100 µl per well of substrate solution containing p-nitrophenyl phosphate. Plates were read at 492 nm.

Drug effects were calculated as a percentage of the reduction in virus in the presence of each drug concentration compared to the titer obtained in the absence of drug. Acyclovir was used as a positive control in all experiments.

(d) Cytotoxicity assays.

Two different assays were used to explore cytotoxicity of selected compounds as we have detailed previously: (i) Cytotoxicity produced in stationary HFF cells was determined by microscopic inspection of cells used in plaque assays which were not affected by the virus [Turk, S. R., et al, *Antimicrob. Agents Chemother.*, 31: 544–550, 1987], and (ii) The effect of compounds during two population doublings of KB cells was determined by crystal violet staining and spectrophotometric quantitation of dye eluted from stained cells [Prichard, M. N., et al, *Antimicrob. Agents Chemother.*, 35:1060–1065, 1991].

(e) Data Analysis.

Dose-response relationships were constructed by linearly regressing the percent inhibition of parameters derived in the preceding sections against logarithm10 drug concentrations. Fifty-percent inhibitory (IC$_{50}$) concentrations were calculated from the regression lines [Goldstein, A., *Biostatistics: An Introductory Text*, MacMillan, New York, pp. 156–161 (1964)]. Samples containing positive controls (acyclovir for HSV-1 and ganciclovir for HCMV) were used in all assays.

(f) Time of Addition Studies.

These studies were performed to compare the mode of action of 4-amino-7-[ (2-methoxyethoxy)methyl]pyrrolo[ 2,3-d]pyrimidine -5-thiocarboxamide (denoted compound 5b or UMJD 828 herein) with the mode of action of 4-amino-5-bromo-7-[(1,3-dihydroxyethyl-2propoxy)methyl]pyrrolo[2,3-d]pyrimidine (compound UMJD 183). Compound UMJD 183 is disclosed in U.S. Pat. No. 4,968, 686 to Townsend et al and is referred to therein as compound 22b or compound 183.

To compare the action of these two pyrrolo[2,3-d]pyrimidines, each drug was added to HCMV-infected HFF cells at different times post-infection. Monolayer cultures of HFF cells were seeded at a final concentration of 1.0×10$^5$ cells per flask in a 24 well culture plate (Costar, Cambridge, Mass.). The cells were allowed to adhere overnight at 37° C. in a humidified 3% CO$_2$/97% air atmosphere. The medium was then removed at which point the cells were infected with HCMV at 0.005 PFU/cell. At 1.5, 6, 12, 24, 36 and 48 hrs, 32µM 5b and 10µM UMJD 183 were added to separate cultures in triplicate (drug solutions of 5b and UMJD 183 were made fresh at each time point). Flasks were incubated for a total of 7 days (time after infection), aliquots of supernatant were removed and diluted, and virus titers were determined on new cultures of HFF cells as described above in section 1(b).

2. Results (a) Antiviral Evaluation.

Compounds were evaluated for activity against human cytomegalovirus (HCMV) and herpes simplex virus type 1 (HSV-1). The cytotoxicity of each compound was determined as detailed above in both human foreskin fibroblasts (HFF cells) and in KB cells. These results are presented in Table 1.

A major factor contributing to the activity of these 7-substituted -4-aminopyrrolo[2,3-d]pyrimidine analogs against HCMV and to a lesser extent HSV-1 is a thioamide moiety at the 5-position. In general, the thioamides were more toxic: than the corresponding nitriles but the cytotoxicity was separated from cytotoxicity. The 7-substituted -4-aminopyrrolo[ 2,3-d]pyrimidine-5-thioamide analogs, 5a–i, afforded the best separation of antiviral activity from cytotoxicity.

The 4-methylamino-5-thioamide derivatives, 10a–b, exhibited antiviral activity; however, the activity was less potent than the corresponding 4-amino-5-thioamide derivatives (Sa, 5b, respectively). Whereas 10b showed slight activity against HSV-1, 10a did not.

Of the 4,6-diamino analogs, the thioamide derivatives 12a–c demonstrated activity against HCMV and HSV-1 and were essentially non-toxic in their antiviral dose range. Interestingly, the corresponding hydroxyethoxymethyl (HEM) and dihydroxy-2-propoxymethyl (DHPM) derivatives were inactive [Swayze, E. E., et al, *Nucleosides and Nucleotides*, 11:1507–1527, 1992].

With regard to the 4,6-.diamino nitrile derivatives, 11a–c, it is clear that a thioamide moiety at the 5-position is not essential for antiviral activity. This is the first case of non-nucleoside derivatives without a thioamide moiety at the 5-position possessing antiviral activity.

(b) Mode of Action Studies

Figure 4:
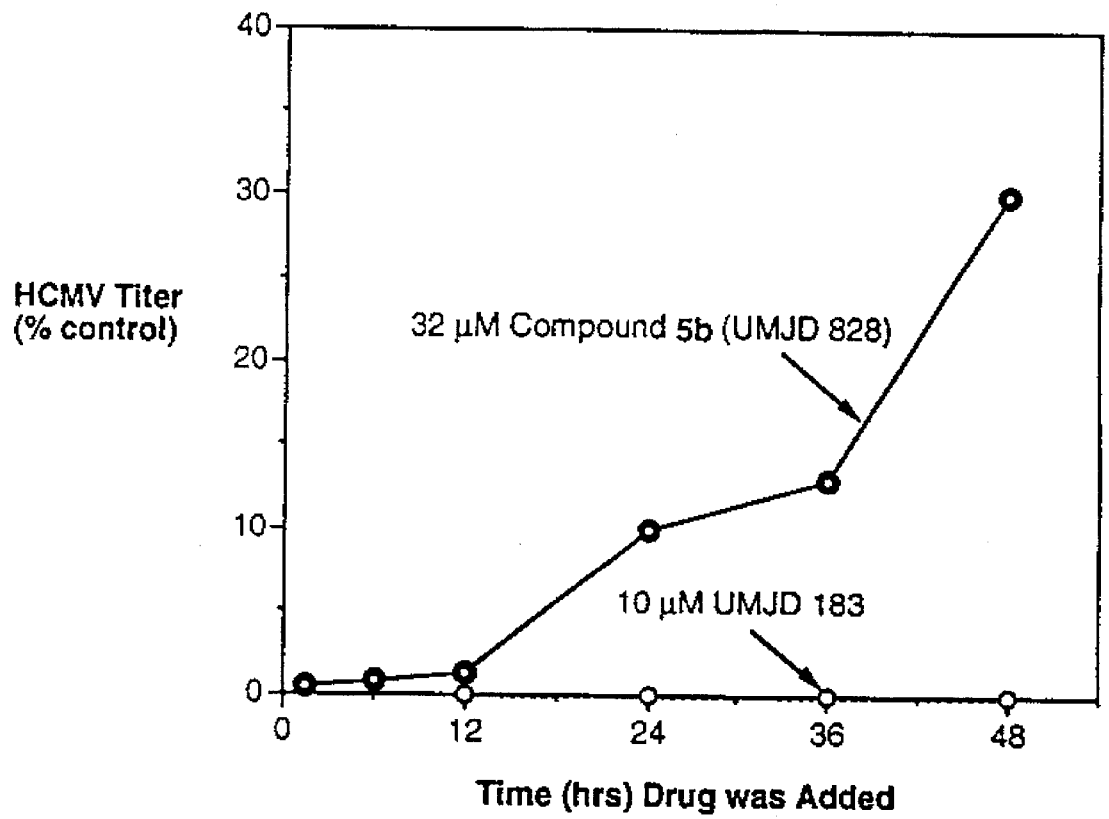
FIG. 4 is a graph for a time of addition study comparing HCMV titer for 4-amino-7-[(2-methoxyethoxy)methyl]pyrrolo[2,3-d]pyrimidine-5-thiocarboxamide (denoted compound 5b herein) and 4-amino-5-bromo-7-[(1,3-dihydroxyethyl-2-propoxy)methyl]-pyrrolo[2,3-d]pyrimidine (compound UMJD 183, disclosed in U.S. Pat. No. 4,968,686 to Townsend et al.).

Time of drug addition studies were performed to compare the mode of action of compound 5b with the mode of action of another pyrrolo[ 2,3-d]pyrimidine that is active against HCMV, compound UMJD 183 [U.S. Pat. No. 4,968,686 to Townsend et al. ]. The latter compound acts by blockage of DNA synthesis via inhibition of HCMV DNA polymerase. Results shown in FIG. 4 demonstrate that compound 5b begins to lose its antiviral effect when added at times later than approximately 12 hr post-infection. In contrast, UMJD 183 produced multiple logarithm$_{10}$ reductions in virus titers when added up to 2 days post-infection. Similar results were obtained when ganciclovir (DHPG) was compared to compound 5b. These results establish that compound 5b acts by a different mechanism than either UMJD 183 or DHPG. Since both DHPG and UMJD 183 are known inhibitors of HCMV DNA synthesis [Biron, K. K., et al., *Proc. Natl. Acad. Sci.*, 82:2473–2477, 1985 and references cited therein] and 5b inhibits before HCMV DNA synthesis has begun, it is clear that compound 5b does not act by inhibition of DNA synthesis. Rather it acts by a unique mechanism which occurs early in the viral replication cycle.

TABLE 1

Antiviral activity and cytotoxicity of 4,5,6,7-substituted pyrrolo[2,3-d]pyrimidines

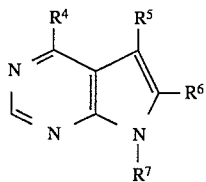

| Compound Number | | Substituent | | | | 50% Inhibitory Concentration$^a$ (μM) | | | |
|---|---|---|---|---|---|---|---|---|---|
| | | | | | | Antiviral Activity | | Cytotoxicity in | |
| Text | UMJD | $R^4$ | $R^5$ | $R^6$ | $R^7$ | HCMV (Plaque) | HSV-1 (ELISA) | HFF Cells (Visual) | KB Cells (Growth) |
| 4g | 836 | $NH_2$ | CN | H | $CH_2C_6H_4$-2-$CH_3$ | 3.4 | >100 | >100 | >100 |
| 5a | 675 | $NH_2$ | $CSNH_2$ | H | $CH_2OCH_2CH_3$ | 2.7 | 22 | >32 | 60 |
| 5b | 828 | $NH_2$ | $CSNH_2$ | H | $CH_2O(CH_2)_2OCH_3$ | 1.2 | 85 | >100 | 165 |
| 5c | 679 | $NH_2$ | $CSNH_2$ | H | $CH_2OCH_2C_6H_5$ | 2.6 | 10 | >100 | 100 |
| 5d | 645 | $NH_2$ | $CSNH_2$ | H | $CH_2C_6H_5$ | 0.4 | 7.4 | >10 | 32 |
| 5e | 648 | $NH_2$ | $CSNH_2$ | H | $CH_2C_6H_4$-4-$CH_3$ | 0.1 | 3.5 | >10 | 32 |
| 5f | 827 | $NH_2$ | $CSNH_2$ | H | $CH_2C_6H_4$-3-$CH_3$ | 0.25 | 15 | >32 | 30 |
| 5g | 837 | $NH_2$ | $CSNH_2$ | H | $CH_2C_6H_4$-2-$CH_3$ | 0.13 | 0.9 | >32 | >17 |
| 5h | 834 | $NH_2$ | $CSNH_2$ | H | $CH_2C_6H_4$-4-t-Bu | 1.5 | 15 | >100 | 7 |
| 5i | 951 | $NH_2$ | $CSNH_2$ | H | $CH_2C_6H_4$-4-$OCH_3$ | 0.1 | >32 | 4 | 28 |
| 10a | 896 | $NHCH_3$ | $CSNH_2$ | H | $CH_2OCH_2CH_3$ | 17 | >100 | >100$^b$ | >100$^b$ |
| 10b | 912 | $NHCH_3$ | $CSNH_2$ | H | $CH_2O(CH_2)_2OCH_3$ | 20 | 30 | >100 | 310$^b$ |
| 11a | 863 | $NH_2$ | CN | $NH_2$ | $CH_2OCH_2CH_3$ | 7.2$^b$ | 100$^b$ | >100$^b$ | 138$^b$ |
| 11b | 864 | $NH_2$ | CN | $NH_2$ | $CH_2O(CH_2)_2OCH_3$ | 8.2b | >100$^b$ | >100$^b$ | 210$^b$ |
| 11c | 862 | $NH_2$ | CN | $NH_2$ | $CH_2OCH_2C_6H_5$ | 2.8$^b$ | 15$^b$ | 100$^b$ | 118$^b$ |
| 12a | 831 | $NH_2$ | $CSNH_2$ | $NH_2$ | $CH_2OCH_2CH_3$ | 16 | 100 | >100 | >320 |
| 12b | 833 | $NH_2$ | $CSNH_2$ | $NH_2$ | $CH_2O(CH_2)_2OCH_3$ | 5 | 100 | >100 | >320 |
| 12c | 832 | $NH_2$ | $CSNH_2$ | $NH_2$ | $CH_2OCH_2C_6H_5$ | 16 | 60 | >100 | 225 |
| Ganciclovir (DHPG) | | | | | | 7.6$^c$ | | >100 | >320 |

$^a$">" indicates IC50 concentration not reached at highest concentration tested.
$^b$Results are the average of two or more experiments.
$^c$Results are the average of 96 experiments.

All patents, patent applications, and publications cited hereinabove are hereby incorporated by reference.

We claim:

1. A compound of the following formula:

wherein $R^4$ is -$NH_2$ or -$NHCH_3$;

$R^5$ is -CN, -$CSNH_2$ or -$CSeNH_2$;

$R^6$ is -H or -$NH_2$; and $R^7$ is selected from the group consisting of
-$CH_2OCH_2CH_3$;
-$CH_2O(CH_2)_2OCH_3$;
-$CH_2OCH_2C_6H_5$;
-$CH_2C_6H_5$;
-$CH_2C_6H_4$-4-$CH_3$;
-$CH_2C_6H_4$-3-$CH_3$;
-$CH_2C_6H_4$-2-$CH_3$;
-$CH_2C_6H_4$-4-$C(CH_3)_3$; and
-$CH_2C_6H_4$-4-$OCH_3$;

with the proviso that if $R^5$ is -CN and $R^6$ is -H then $R^4$ is -$NH_2$ and $R^7$ is -$CH_2C_6H_4$-2-$CH_3$; and pharmaceutically acceptable salts thereof.

2. The compound of claim 1, wherein $R^5$ is -CN or -$CSNH_2$.

3. The compound of claim 1, wherein $R^4$ is -$NH_2$ or -$NHCH_3$, $R^5$ is -$CSNH_2$, and $R^6$ is -H or -$NH_2$.

4. The compound of claim 1, wherein $R^4$ is -$NH_2$ or -$NHCH_3$, $R^5$ is -CN, and $R^6$ is -$NH_2$.

5. The compound of claim 1, wherein $R^4$ is -$NH_2$, $R^5$ is -$CSNH_2$, and $R^6$ is -$NH_2$.

6. The compound of claim 1, wherein $R^4$ is -$NH_2$; $R^5$ is -$CSNH_2$; and $R^6$ is -H.

7. The compound of claim 1, wherein $R^4$ is -$NH_2$; $R^5$ is -CN; and $R^6$ is -$NH_2$.

8. The compound of claim 1, wherein $R^4$ is -$NHCH_3$; $R^5$ is -$CSNH_2$; and $R^6$ is -H.

9. The compound of claim 1, wherein:

$R^4$ is -$NH_2$; $R^5$ is -CN; $R^6$ is -H; and $R^7$ is -$CH_2C_6H_4$-2-$CH_3$ (4g);

$R^4$ is -$NH_2$; $R^5$ is -$CSNH_2$; $R^6$ is -H; and $R^7$ is -$CH_2OCH_2CH_3$ (5a);

$R^4$ is -$NH_2$; $R^5$ is -$CSNH_2$; $R^6$ is -H; and $R^7$ is -$CH_2O(CH_2)_2OCH_3$ (5b);

$R^4$ is -$NH_2$; $R^5$ is -$CSNH_2$; $R^6$ is -H; and $R^7$ is -$CH_2OCH_2C_6H_5$ (5c);

$R^4$ is -$NH_2$; $R^5$ is -$CSNH_2$; $R^6$ is -H; and $R^7$ is -$CH_2C_6H_5$ (5d);

$R^4$ is -$NH_2$; $R^5$ is -$CSNH_2$; $R^6$ is -H; and $R^7$ is -$CH_2C_6H_4$-4 -$CH_3$ (5e);

$R^4$ is -$NH_2$; $R^5$ is -$CSNH_2$; $R^6$ is -H; and $R^7$ is -$CH_2C_6H_4$-3-$CH_3$ (5f);

$R^4$ is -$NH_2$; $R^5$ is -$CSNH_2$; $R^6$ is -H; and $R^7$ is -$CH_2C_6H_4$-2-$CH_3$ (5g);

$R^4$ is -$NH_2$; $R^5$ is -$CSNH_2$; $R^6$ is -H; and $R^7$ is -$CH_2C_6H_4$-4-$C(CH_3)_3$ (5h);

$R^4$ is -$NH_2$; $R^5$ is -$CSNH_2$; $R^6$ is -H; and $R^7$ is -$CH_2C_6H_4$-4-$OCH_3$ (5i);

$R^4$ is -$NHCH_3$; $R^5$ is -$CSNH_2$; $R^6$ is -H; and $R^7$ is -$CH_2OCH_2CH_3$ (10a);

$R^4$ is -$NHCH_3$; $R^5$ is -$CSNH_2$; $R^6$ is -H; and $R^7$ is -$CH_2O(CH_2)_2OCH_3$ (10b);

$R^4$ is -$NH_2$; $R^5$ is -CN; $R^6$ is -$NH_2$; and $R^7$ is -$CH_2OCH_2CH_3$ (11a);

$R^4$ is -$NH_2$; $R^5$ is -CN; $R^6$ is -$NH_2$ and $R^7$ is -$CH_2O(CH_2)_2OCH_3$ (11b);

$R^4$ is -$NH_2$; $R^5$ is -CN; $R^6$ is -$NH_2$; and $R^7$ is -$CH_2OCH_2C_6H_5$ (11c);

$R^4$ is -$NH_2$; $R^5$ is -CN; $R^6$ is -$CSNH_2$; and $R^7$ is -$CH_2OCH_2CH_3$ (12a);

$R^4$ is -$NH_2$; $R^5$ is -CN; $R^6$ is -$CSNH_2$; and $R^7$ is -$CH_2O(CH_2)_2OCH_3$ (12b); and $R^4$ is -$NH_2$; $R^5$ is -CN; $R^6$ is -$CSNH_2$; and $R^7$ is -$CH_2OCH_2C_6H_5$ (12c).

10. The compound of claim 1, wherein $R^4$ is -$NH_2$, $R^5$ is -CN, $R^6$ is -H and $R^7$ is -$CH_2C_6H_4$-2-$CH_3$ (4g).

11. The compound of claim 1, wherein $R^4$ is -$NH_2$, $R^5$ is -$CSNH_2$, $R^6$ is -H and $R^7$ is -$CH_2OCH_2CH_3$ (5a).

12. The compound of claim 1, wherein $R^4$ is -$NH_2$, $R^5$ is -$CSNH_2$, $R^6$ is -H and $R^7$ is -$CH_2O(CH_2)_2OCH_3$ (5b).

13. The compound of claim 1, wherein $R^4$ is -$NH_2$, $R^5$ is -$CSNH_2$, $R^6$ is -H and $R^7$ is -$CH_2OCH_2C_6H_5$ (5c).

14. The compound of claim 1, wherein $R^4$ is -$NH_2$, $R^5$ is -$CSNH_2$, $R^6$ is -H and $R^7$ is -$CH_2C_6H_5$ (5d).

15. The compound of claim 1, wherein $R^4$ is -$NH_2$, $R^5$ is -$CSNH_2$, $R^6$ is -H and $R^7$ is -$CH_2C_6H_4$-4-$CH_3$ (5e).

16. The compound of claim 1, wherein $R^4$ is -$NH_2$, $R^5$ is -$CSNH_2$, $R^6$ is -H and $R^7$ is -$CH_2C_6H_4$-3-$CH_3$ (5f).

17. The compound of claim 1, wherein $R^4$ is -$NH_2$, $R^5$ is -$CSNH_2$, $R^8$ is -H and $R^7$ is -$CH_2C_6H_4$-2-$CH_3$ (5g).

18. The compound of claim 1, wherein $R^4$ is -$NH_2$, $R^5$ is -$CSNH_2$, $R^6$ is -H and $R^7$ is -$CH_2C_6H_4$-4-$C(CH_3)_3$ (5h).

19. The compound of claim 1, wherein $R^4$ is -$NH_2$, $R^5$ is -$CSNH_2$, $R^6$ is -H and $R^7$ is -$CH_2C_6H_4$-4-$OCH_3$ (5i).

20. The compound of claim 1, wherein $R^4$ is -$NHCH_3$, $R^5$ is -$CSNH_2$, $R^6$ is -H and $R^7$ is -$CH_2OCH_2CH_3$ (10a).

21. The compound of claim 1, wherein $R^4$ is -$NHCH_3$, $R^5$ is -$CSNH_2$, $R^6$ is -H and $R^7$ is -$CH_2O(CH_2)_2OCH_3$ (10b).

22. The compound of claim 1, wherein $R^4$ is -$NH_2$, $R^5$ is -CN, $R^6$ is -$NH_2$ and $R^7$ is -$CH_2OCH_2CH_3$ (11a).

23. The compound of claim 1, wherein $R^4$ is -$NH_2$, $R^5$ is -CN, $R^6$ is -$NH_2$ and $R^7$ is -$CH_2O(CH_2)_2OCH_3$ (11b).

24. The compound of claim 1, wherein $R^4$ is -$NH_2$, $R^5$ is -CN, $R^6$ is -$NH_2$ and $R^7$ is -$CH_2OCH_2C_6H_5$ (11c).

25. The compound of claim 1, wherein $R^4$ is -$NH_2$, $R^5$ is -$CSNH_2$, $R^6$ is -$NH_2$ and $R^7$ is -$CH_2OCH_2CH_3$ (12a).

26. The compound of claim 1, wherein $R^4$ is -$NH_2$, $R^5$ is -$CSNH_2$, $R^6$ is -$NH_2$ and $R^7$ is -$CH_2O(CH_2)_2OCH_3$ (12b).

27. The compound of claim 1, wherein $R^4$ is -$NH_2$, $R^5$ is -$CSNH_2$, $R^6$ is -$NH_2$ and $R^7$ is -$CH_2OCH_2C_6H_5$ (12c).

28. A pharmaceutical composition for treating viral infections comprising a therapeutically effective amount of one or more compounds of the following formula:

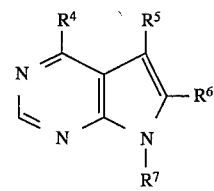

wherein
$R^4$ is -$NH_2$ or -$NHCH_3$;
$R^5$ is -CN, -$CSNH_2$, or -$CSeNH_2$;
$R^6$ is -H or -$NH_2$; and
$R^7$ is selected from the group consisting of
-$CH_2OCH_2CH_3$;
-$CH_2O(CH_2)_2OCH_3$;
-$CH_2OCH_2C_6H_5$;
-$CH_2C_6H_5$;
-$CH_2C_6H_4$-4-$CH_3$;
-$CH_2C_6H_4$-3-$CH_3$;
-$CH_2C_6H_4$-2-$CH_3$;
-$CH_2C_6H_4$-4-$C(CH_3)_3$; and
-$CH_2C_6H_4$-4-$OCH_3$;
with the proviso that if $R^5$ is -CN and $R^6$ is -H then $R^4$ is -$NH_2$ and $R^7$ is -$CH_2C_6H_4$-2-$CH_3$;
and a pharmaceutically acceptable carrier.

29. The pharmaceutical composition of claim 28 wherein $R^5$ is -CN or -$CSNH_2$.

30. A method for treating an HCMV or HSV-1 viral infection in an animal patient comprising administering a therapeutically effective amount of one or more compounds of the following formula:

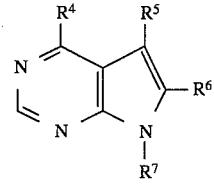

wherein
$R^4$ is -$NH_2$ or -$NHCH_3$;
$R^5$ is -CN, -$CSNH_2$, or -$CSeNH_2$;
$R^6$ is -H or -$NH_2$; and
$R^7$ is selected from the group consisting of
-$CH_2OCH_2CH_3$;
-$CH_2O(CH_2)_2OCH_3$;
-$CH_2OCH_2C_6H_5$;
-$CH_2C_6H_5$;
-$CH_2C_6H_4$-4-$CH_3$;
-$CH_2C_6H_4$-3-$CH_3$;
-$CH_2C_6H_4$-2-$CH_3$;
-$CH_2C_6H_4$-4-$C(CH_3)_3$; and
-$CH_2C_6H_4$-4-$OCH_3$;
with the proviso that if $R^5$ is -CN and $R^6$ is -H then $R^4$ is -$NH_2$ and $R^7$ is -$CH_2C_6H_2$-2-$CH_3$.

31. The method for treating a viral infection of claim 30 wherein $R^5$ is -CN or -$CSNH_2$.

* * * * *

UNITED STATES PATENT AND TRADEMARK OFFICE
CERTIFICATE OF CORRECTION

PATENT NO. : 5,543,413
DATED : August 6, 1996
INVENTOR(S) : Leroy B. Townsend, et. al.

It is certified that error appears in the above-indentified patent and that said Letters Patent is hereby corrected as shown below:

The last six (6) printed lines of issued claim 9, at column 29, lines 17-22, should read:

"$R^4$ is -$NH_2$; $R^5$ is -$CSNH_2$; $R^6$ is -$NH_2$; and $R^7$ is -$CH_2OCH_2CH_3$ (12a);

$R^4$ is -$NH_2$; $R^5$ is -$CSNH_2$; $R^6$ is -$NH_2$; and $R^7$ is -$CH_2O(CH_2)_2OCH_3$ (12b); and $R^4$ is -$NH_2$; $R^5$ is -$CSNH_2$; $R^6$ is -$NH_2$; and $R^7$ is -$CH_2OCH_2C_6H_5$ (12c)."

Signed and Sealed this

Twenty-sixth Day of November 1996

Attest:

BRUCE LEHMAN

*Attesting Officer*     *Commissioner of Patents and Trademarks*